(12) United States Patent
Tripp

(10) Patent No.: US 10,919,961 B2
(45) Date of Patent: Feb. 16, 2021

(54) METHODS AND COMPOSITIONS FOR TREATING ASTHMA USING ANTI-IL-13 ANTIBODIES

(71) Applicant: AbbVie, Inc., North Chicago, IL (US)

(72) Inventor: Catherine Tripp, Worcester, MA (US)

(73) Assignee: Abbvie, Inc., North Chicago, IL (US)

( * ) Notice: Subject to any disclaimer, the term of this patent is extended or adjusted under 35 U.S.C. 154(b) by 0 days.

(21) Appl. No.: 15/633,936

(22) Filed: Jun. 27, 2017

(65) Prior Publication Data

US 2018/0079808 A1 Mar. 22, 2018

Related U.S. Application Data

(63) Continuation of application No. 14/232,356, filed as application No. PCT/US2012/045268 on Jul. 2, 2012, now abandoned.

(60) Provisional application No. 61/507,347, filed on Jul. 13, 2011.

(51) Int. Cl.
| | | |
|---|---|---|
| C07K 16/24 | (2006.01) | |
| A61K 39/395 | (2006.01) | |
| A61K 45/06 | (2006.01) | |
| A61K 39/00 | (2006.01) | |

(52) U.S. Cl.
CPC ........ *C07K 16/244* (2013.01); *A61K 39/3955* (2013.01); *A61K 45/06* (2013.01); *A61K 2039/505* (2013.01)

(58) Field of Classification Search
None
See application file for complete search history.

(56) References Cited

U.S. PATENT DOCUMENTS

| | | |
|---|---|---|
| 2008/0171014 A1 | 7/2008 | Wu et al. |
| 2009/0068195 A1 | 3/2009 | Vugmeyster et al. |
| 2009/0226530 A1 | 9/2009 | Lassner et al. |
| 2010/0233079 A1 | 9/2010 | Jakob et al. |
| 2011/0165066 A1 | 7/2011 | Wu et al. |
| 2014/0341913 A1 | 11/2014 | Tripp |

FOREIGN PATENT DOCUMENTS

| | | |
|---|---|---|
| EP | 2292660 A2 | 3/2011 |
| EP | 2314624 A2 | 4/2011 |
| WO | 2007/036745 A2 | 4/2007 |
| WO | 2008/086395 A2 | 7/2008 |
| WO | 2011/032148 A1 | 3/2011 |

OTHER PUBLICATIONS

Singh et al, BMC Pulmonary Medicine, Jan. 2010, vol. 10, No. 3, pp. 1-8.*
Garry M. Walsh, Current Opinion in Investigational Drugs; Oct. 31, 2010, vol. 11, No. 11, pp. 1305-1312.*
Brorson et al., Mutational analysis of avidity and fine specificity of anti-levan antibodies. J Immunol. Dec. 15, 1999;163(12):6694-6701.
Brummell et al., Probing the Combining Site of an Anti-Carbohydrate Antibody by Saturation-Mutagenesis: Role of the Heavy-Chain CDR3 Residues. Biochemistry. 1993;32:1180-1187.
Colman, Effects of amino acid sequence changes on antibody-antigen interactions. Res Immunol. Jan. 1994;145(1):33-36.
Kobayashi et al., Tryptophan H33 plays an important role in pyrimidine (6-4) pyrimidone photoproduct binding by a high-affinity antibody. Protein Eng. Oct. 1999;12(10):879-884.
Nials et al., Mouse models of allergic asthma: acute and chronic allergen challenge. Dis Model Mech. Nov.-Dec. 2008;1(4-5):213-220.
Oh et al., An open label single-dose bioavailability study of the pharmacokinetics of CAT-354 after subcutaneous and intravenous administration in healthy males. British J. Clin. Pharmacol. 2010;69(6):645-655.
Scheerens et al., Predictive and Pharmacodynamic Biomarkers of Interleukin-13 blockade: Effect of Lebrikizumab on Late Phase Asthmatic Response to Allergen Challenge. J Allergy Clin Immunol. Feb. 2011;AB164, Abstract No. 624. 1 pages.
Singh et al., A phase 1 study evaluating the pharmacokinetics, safety and tolerability of repeat dosing with a human IL-13 antibody (CAT-354) in subjects with asthma. BMC Pulm Med. Jan. 8, 2010;10:3. 8 pages.
Vugmeyster et al., Preclinical pharmacokinetics, interspecies scaling, and tissue distribution of humanized monoclonal anti-IL-13 antibodies with different IL-13 neutralization mechanisms. International Immunopharmacology. 2008;8(3):477-483.
Walsh, Tralokinumab, an anti-IL-13 mAb for the potential treatment of asthma and COPD. Curr Opin Investig Drugs. Nov. 2010;11(11):1305-1312.
International Search Report and Written Opinion for Application No. PCT/US2012/045268, dated Jan. 10, 2013 16 pages.
International Preliminary Report on Patentability for Application No. PCT/US2012/045268, dated Aug. 2, 2013. 19 pages.
Examination Report dated Aug. 31, 2017 based on co-pending Austrlian Application No. 2012283039—3 Pages.
Examination Report dated Sep. 8, 2017 based on co-pending European Application No. 12811052.5—8 Pages.
Decision to Refuse a European Patent Application pertaining to co-pending European Patent Application No. 12811052.5 dated May 2, 2019, Titled: Methods and Compositions for Treating Asthma Using Anti-IL-13 Antibodies, 35 Pages.
Dostalek, Miroslav, et al., "Pharmacokinetics, Pharmacodynamics and Physiologically-Based Pharmacokinetic Modelling of Monoclonal Antibodies", Clinical Pharmacokinetics, Jan. 9, 2013, vol. 51, pp. 83-124.
Keizer, Ron J., et al., "Clinical Pharmacokinetics of Therapeutic Monoclonal Antibodies", Clinical Pharmacokinetics, 2010, vol. 49, No. 8, pp. 493-507.
Wang, W., et al., "Monoclonal Antibody Pharmacokinetics and Pharmacodynamics", Nature Publishing Group, Nov. 2008, vol. 84, No. 5, pp. 548-558.

* cited by examiner

*Primary Examiner* — Bridget E Bunner
*Assistant Examiner* — Fozia Hamud
(74) *Attorney, Agent, or Firm* — McCarter & English, LLP

(57) ABSTRACT

The invention provides methods and compositions for treating asthma, e.g., mild or moderate asthma, in a subject using an anti-IL-13 antibody, or antigen-binding portion thereof.

12 Claims, 12 Drawing Sheets

Specification includes a Sequence Listing.

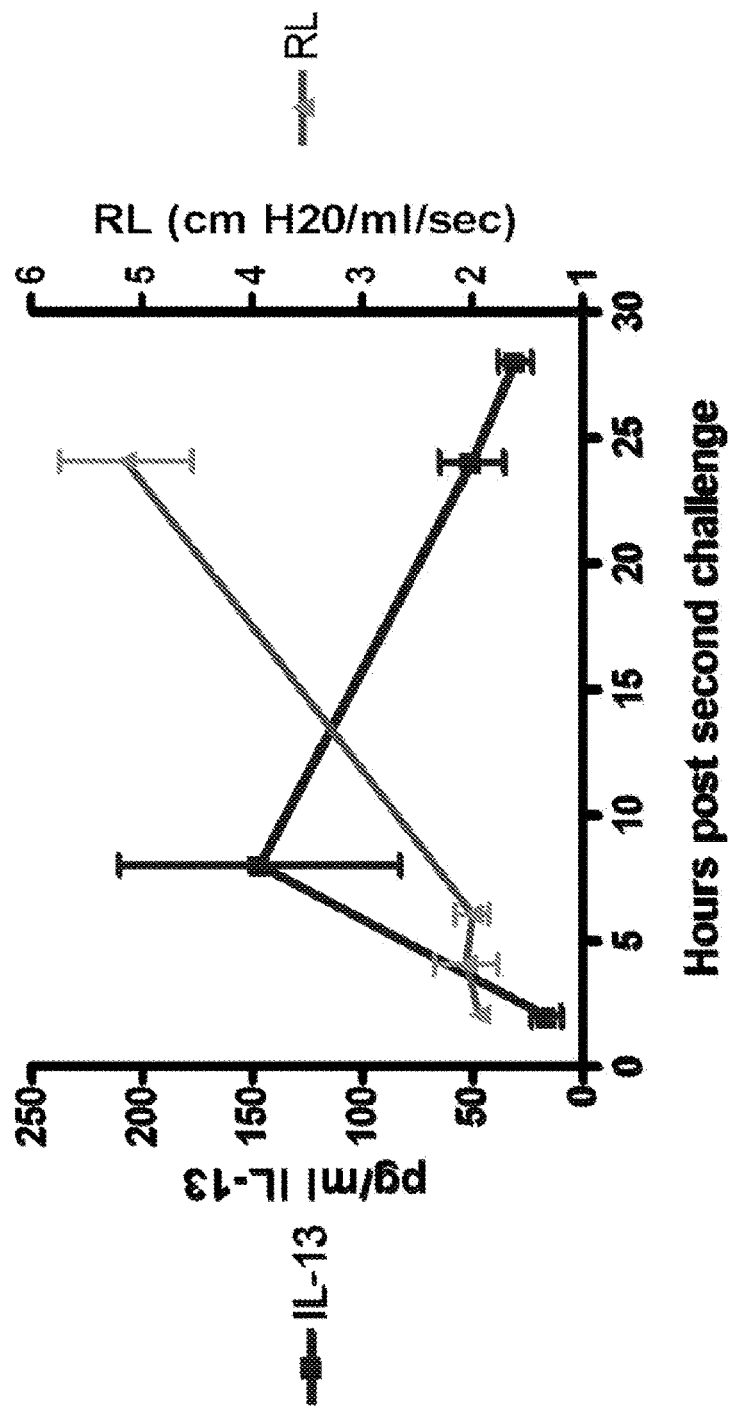
Figure 1: IL-13 Expression Precedes Pulmonary Dysfunction

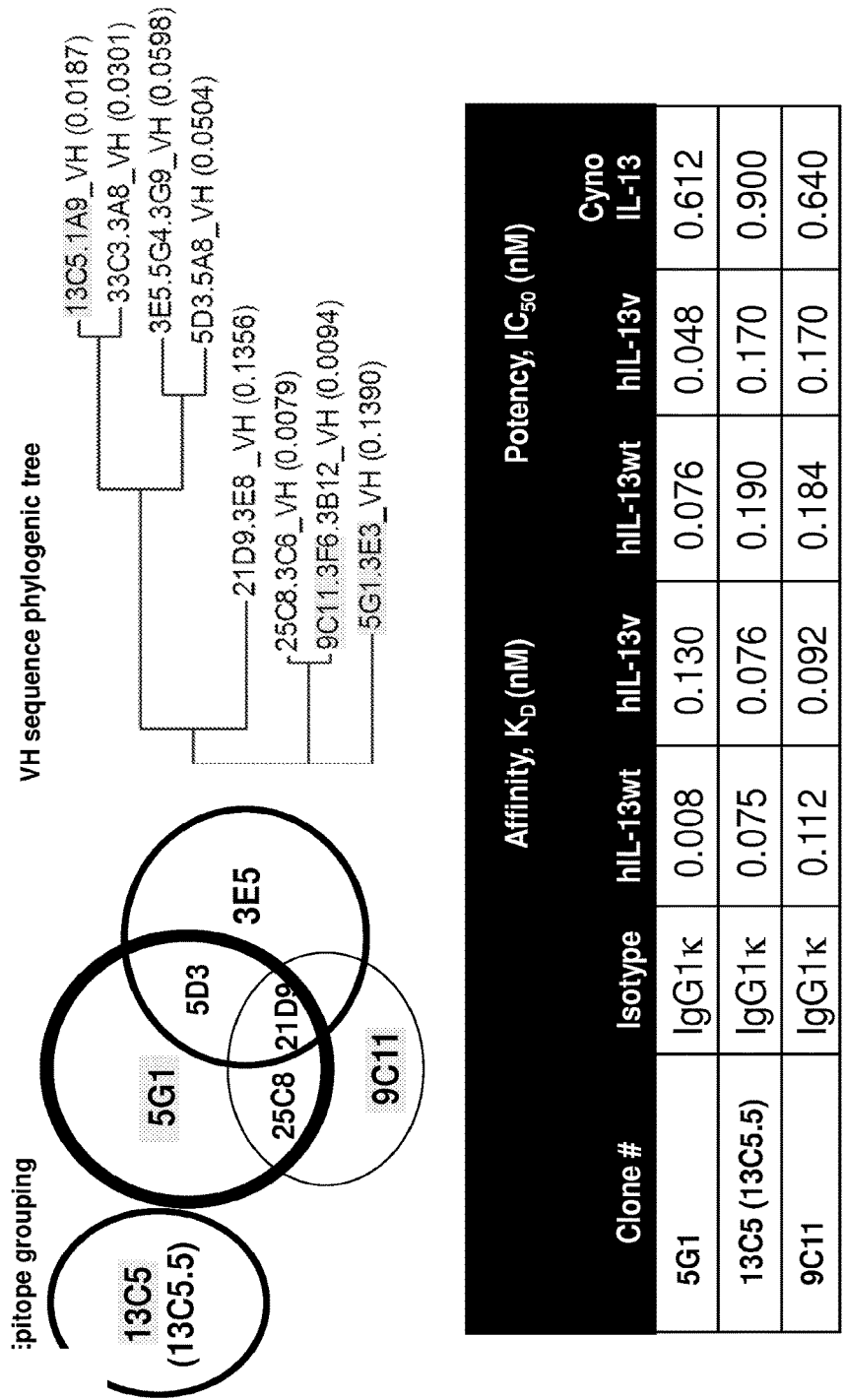
Figure 2: 13C5.5 is Derived from a Hybridoma with a Unique Epitope and Lineage

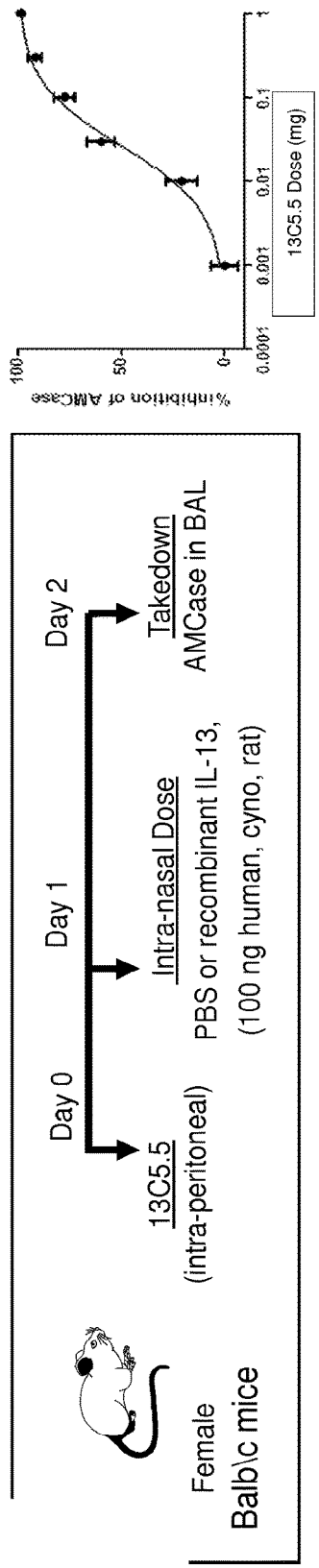
Figure 3: 13C5.5 Neutralizes IL-13 in the Lung

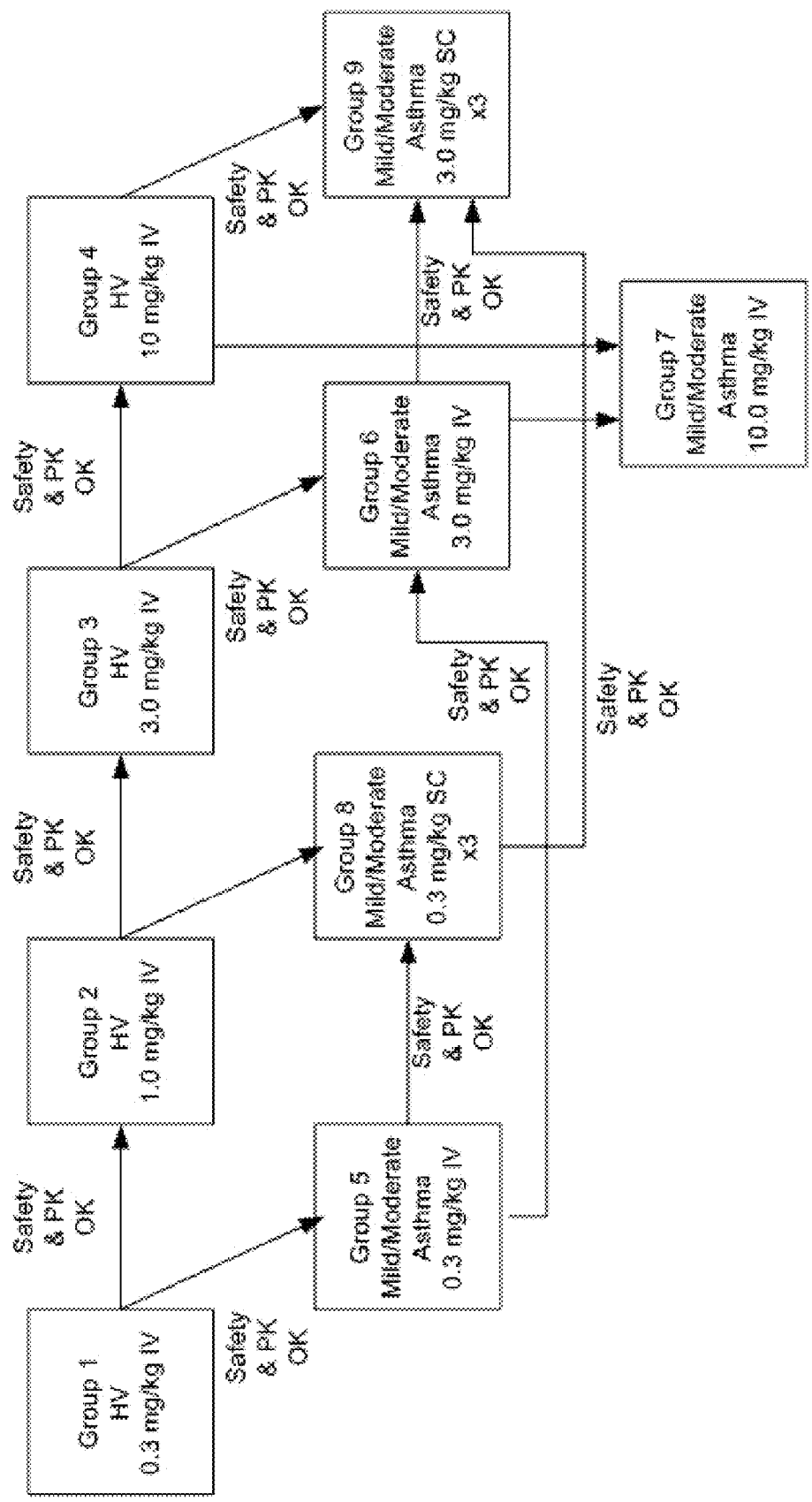
Figure 4: Schematic of First-in-Human (FIH) Dosing

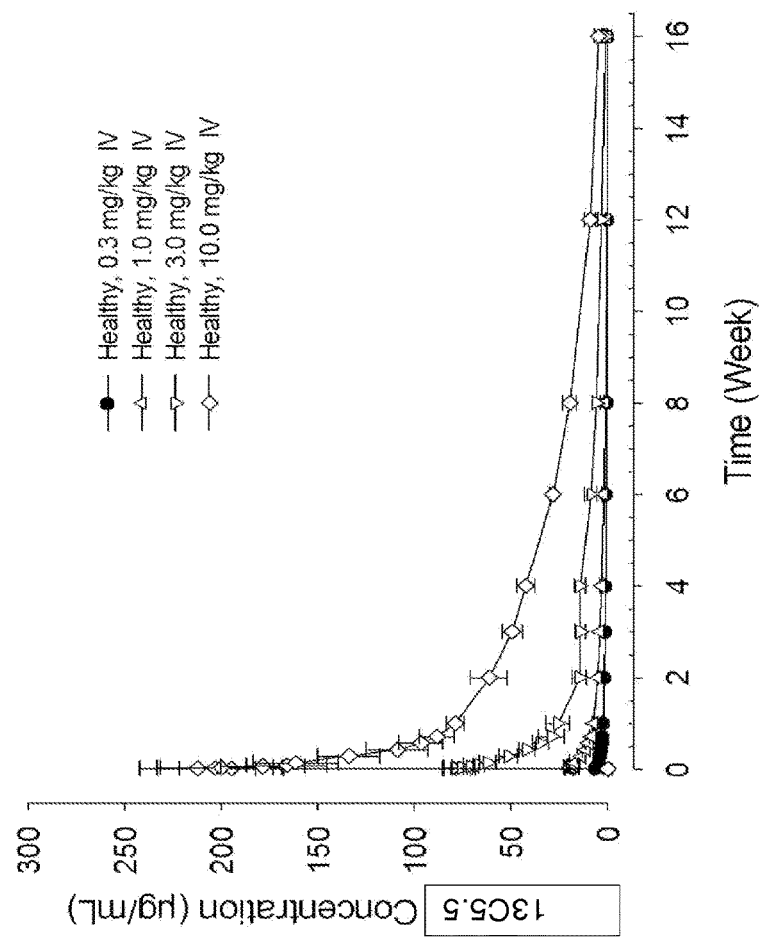
Figure 5: Mean ± SD 13C5.5 Serum Concentration-Time Profiles After Single 0.3 mg/kg, 1.0 mg/kg, 3.0 mg/kg and 10 mg/kg IV Infusions of 13C5.5 to Healthy Subjects, Linear Scale

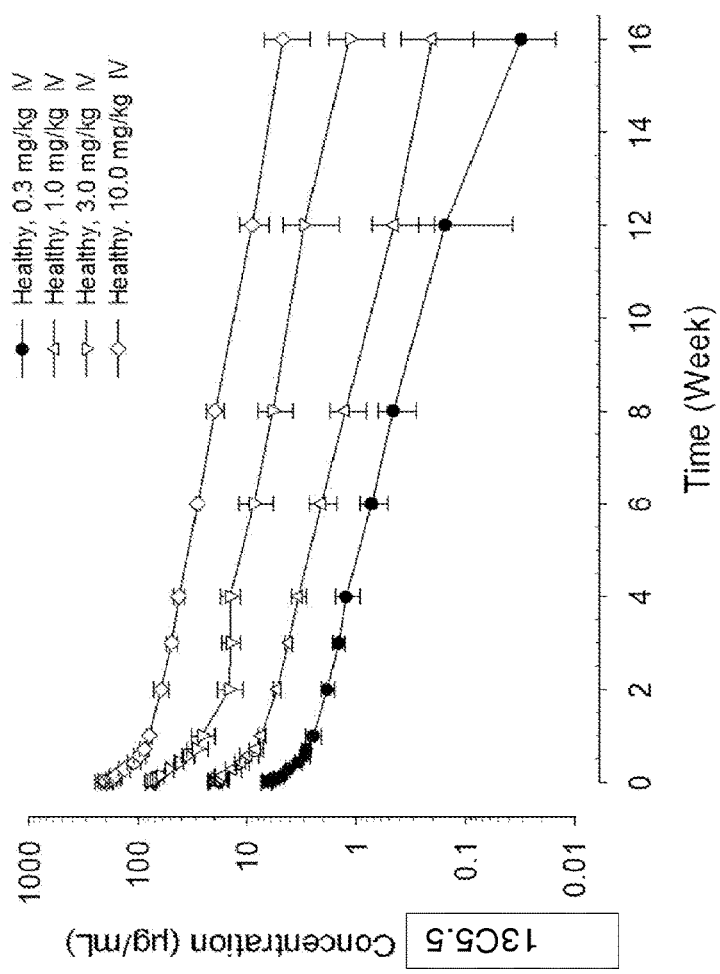
Figure 6: Pharmacokinetic Parameters of 13C5.5
- Pharmacokinetics were dose linear over the range in HV

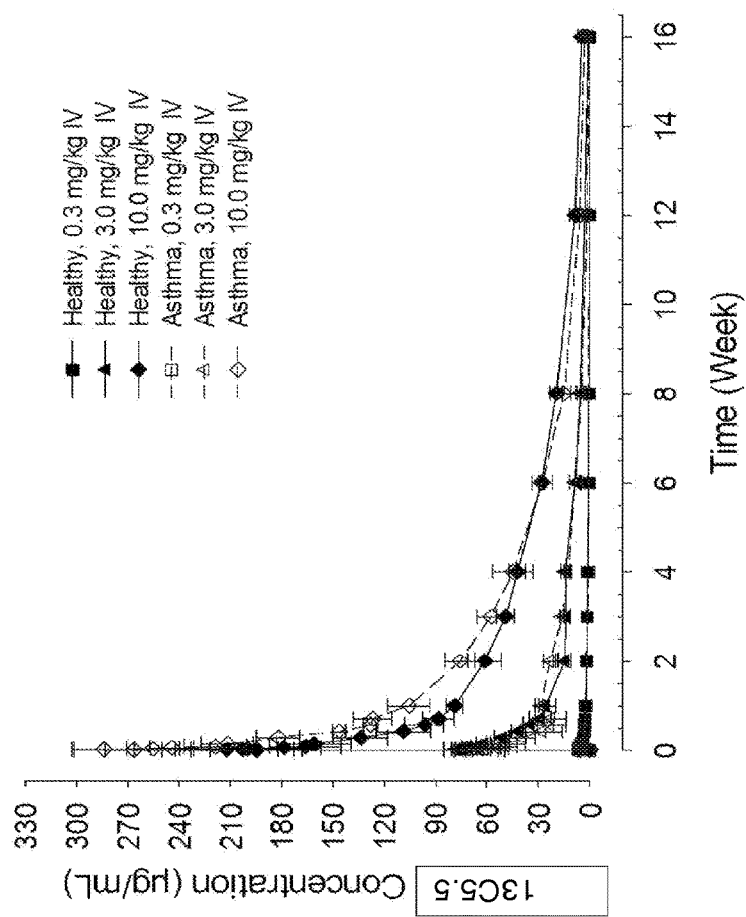
Figure 7: Mean ± SD 13C5.5 Serum Concentration-Time Profiles Following Single 0.3 mg/kg, 3.0 mg/kg and 10 mg/kg IV Infusions of 13C5.5 to Healthy and Asthma Subjects, Linear Scale

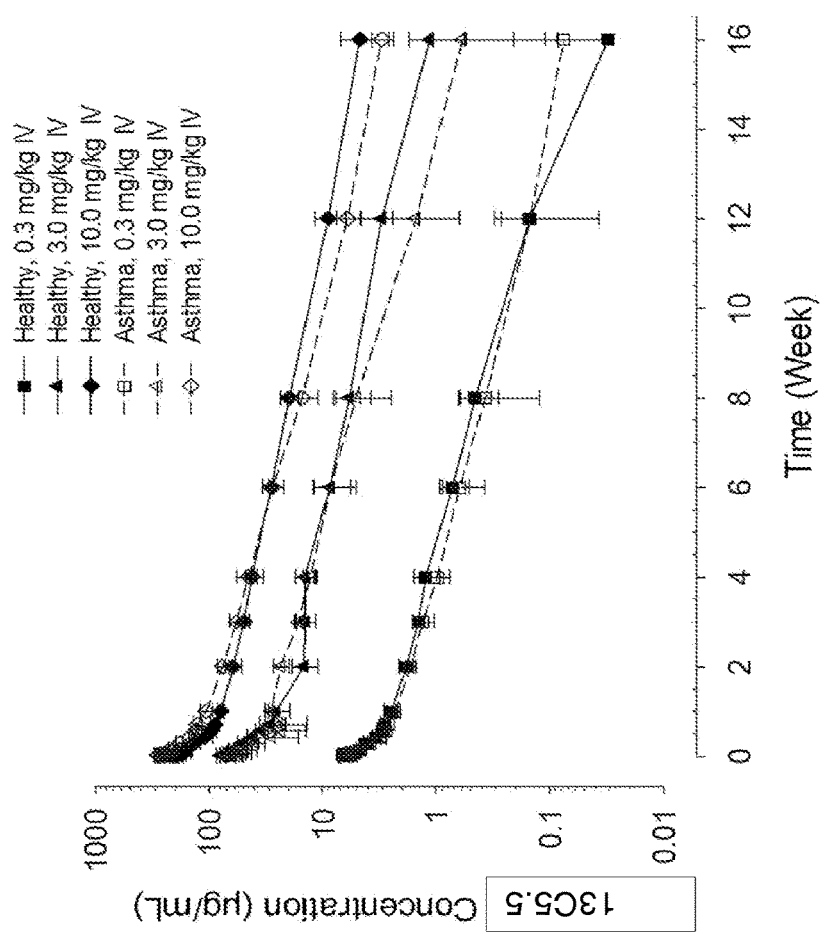
Figure 8: Pharmacokinetic Parameters of 13C5.5
harmacokinetics were similar between HV and subjects with mild/moderate asthma
ean half-life ranges from approximately 16.2 ± 9.24 days to 26.0 ± 4.93 day

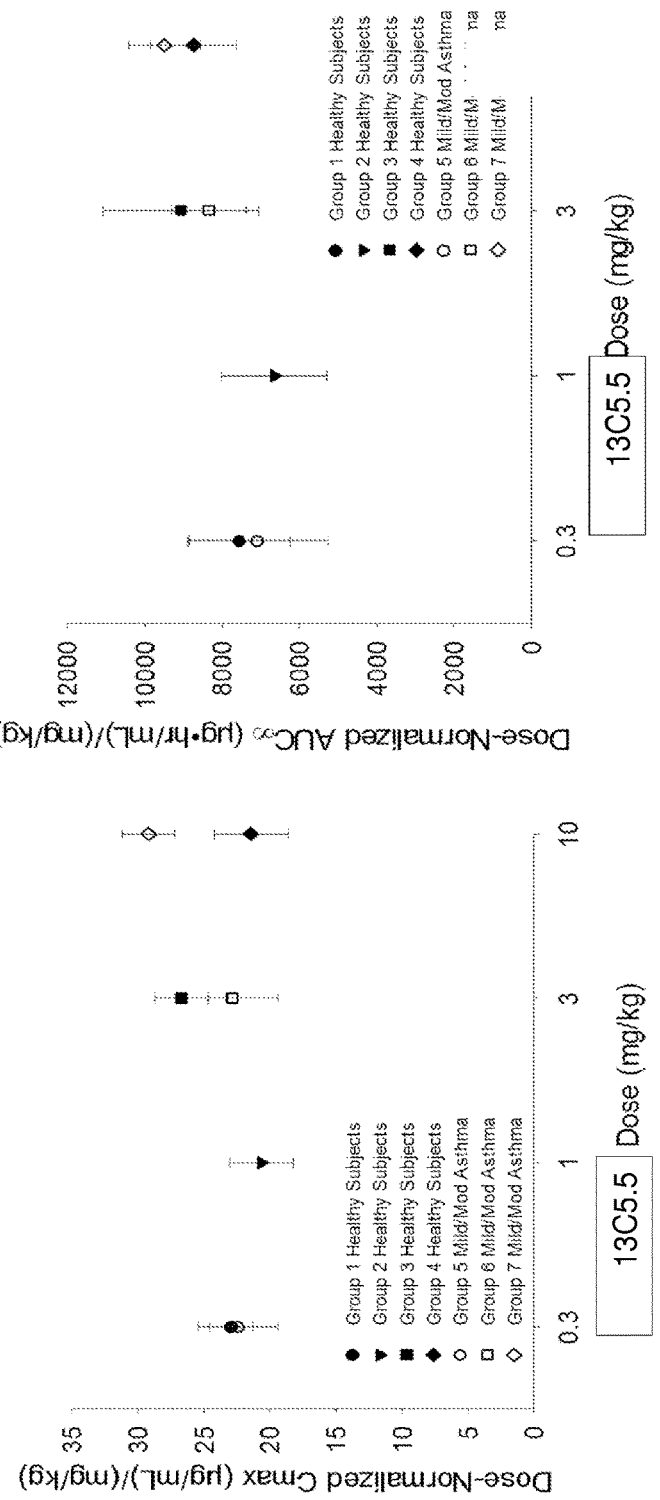
Figure 9: Pharmacokinetic Parameters of 13C5.5

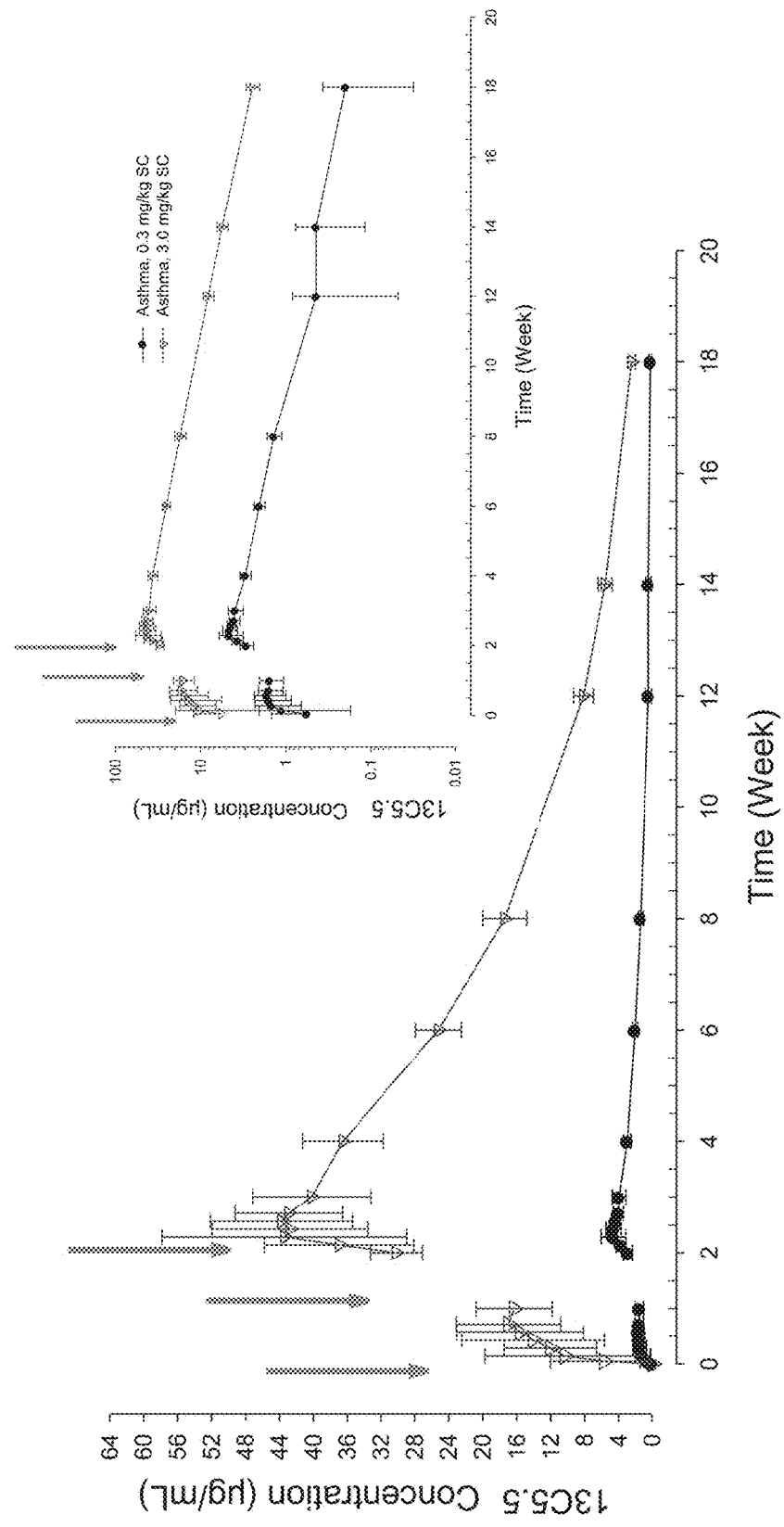

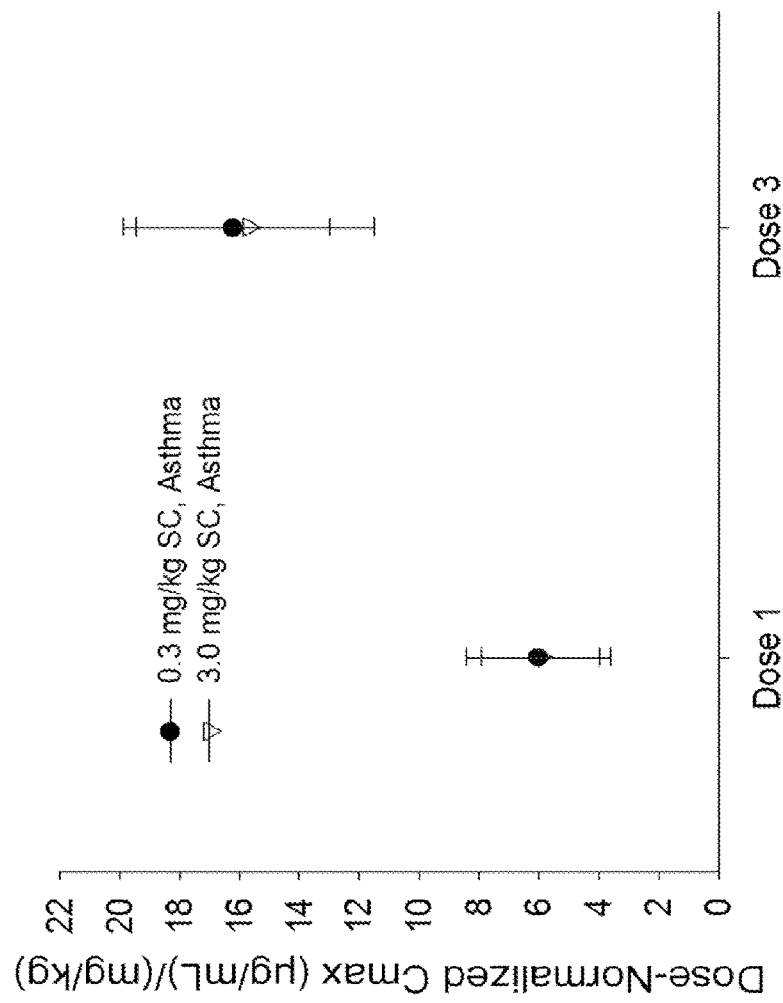
Figure 11: Mean ± SD Dose Normalized Cmax Values Following 3 Weekly 0.3 mg/kg (Group 8) and 3.0 mg/kg (Group 9) SC Injections of 13C5.5 (Part 3)

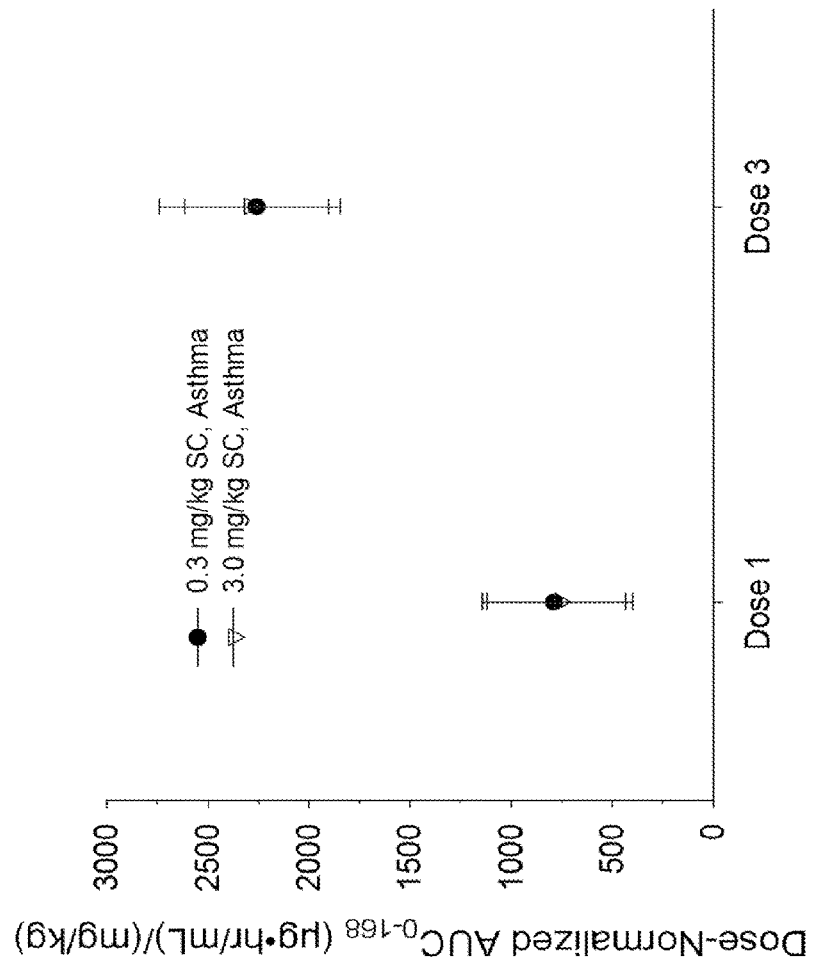
Figure 12: Mean ± SD Dose Normalized AUC0-168 Values Following 3 Weekly 0.3 mg/kg (Group 8) and 3.0 mg/kg (Group 9) SC Injections of 13C5.5 (Part 3)

METHODS AND COMPOSITIONS FOR TREATING ASTHMA USING ANTI-IL-13 ANTIBODIES

RELATED APPLICATIONS

This application is a continuation application of U.S. application Ser. No. 14/232,356, filed May 27, 2014 which, in turn, is a 35 U.S.C. § 371 national stage filing of International Application No. PCT/US2012/045268, filed Jul. 2, 2012, which, in turn claims priority to U.S. Provisional Ser. No. 61/507,347 filed Jul. 13, 2011. The entire contents of each of the foregoing applications are incorporated herein by reference.

BACKGROUND OF THE INVENTION

Asthma is a chronic inflammatory disorder of the airways characterized by wheezing, breathlessness, chest tightness, and cough. Asthma affects approximately 20 million people in the US, and about 75% of asthma patients are adults. Of the adult asthma patients, approximately 60% of asthma patients have mild disease, about 20% have moderate disease and the remaining 20% have severe disease.

Interleukin-13 (IL-13) is thought to be pivotal in the pathogenesis of human asthma, in that elevated levels of IL-13 are present in the lungs of asthma patients, and these levels correlate with disease severity (FIG. 1). Likewise, increased IL-13 is present in both sputum and in lung biopsies of patients with moderate to severe asthma who are treated with inhaled corticosteroids (ICS) or systemic corticosteroids and continue to be symptomatic. Moreover, human IL-13 genetic polymorphisms are associated with asthma and atopy (allergic hypersensitivity). IL-13 binds to two receptors, IL-13Rα1 and IL-13Rα2. IL-13 is a well-validated target for asthma as efficacy has been demonstrated using various means of IL-13 antagonism in multiple, pre-clinical models of asthma.

Due to the role of human IL-13 in a variety of human disorders, therapeutic strategies have been designed to inhibit or counteract IL-13 activity. In particular, antibodies that bind to, and neutralize, IL-13 have been sought as a means to inhibit IL-13 activity. However, there exists a need in the art for improved antibodies capable of binding IL-13 for treating asthma.

SUMMARY OF THE INVENTION

The present invention provides methods and compositions for treating asthma, e.g., mild or moderate asthma, using an anti-IL-13 antibody, or antigen-binding portion thereof.

In one aspect, the invention provides an isolated composition comprising an anti-IL-13 antibody, or antigen-binding portion thereof, wherein, when administered intravenously to a subject at a dose of about 0.3 mg/kg, the antibody, or antigen-binding portion thereof, is capable of exhibiting: (a) an area under the curve (AUC) of between about 1,500 and about 2,700 µgh/ml; (b) a volume of distribution of between about 65 and 125 mL/kg; (c) a peak concentration ($C_{max}$) of between about 5 and about 8 µg/ml; and (d) a clearance rate of between about 0.1 and about 0.2 ml/h/kg.

In another aspect, the invention provides an isolated composition comprising an anti-IL-13 antibody, or antigen-binding portion thereof, wherein, when administered intravenously to a subject at a dose of about 3 mg/kg, the antibody, or antigen-binding portion thereof, is capable of exhibiting: (a) an area under the curve (AUC) of between about 21,000 and about 33,500 µgh/ml; (b) a volume of distribution of between about 55 and about 100 mL/kg; (c) a peak concentration ($C_{max}$) of between about 55 and about 90 µg/ml; and (d) a clearance rate of between about 0.08 and about 0.15 ml/h/kg.

In another aspect, the invention provides an isolated composition comprising an anti-IL-13 antibody, or antigen-binding portion thereof, wherein, when administered intravenously to a subject at a dose of about 10 mg/kg, the antibody, or antigen-binding portion thereof, is capable of exhibiting: (a) an area under the curve (AUC) of between about 75 and about 100 µgh/ml; (b) a volume of distribution of between about 90 and about 130 mL/kg; (c) a peak concentration ($C_{max}$) of between about 185 and about 250 µg/ml; and (d) a clearance rate of between about 0.1 and about 0.15 ml/h/kg.

In yet another aspect, the invention provides an isolated composition comprising an anti-IL-13 antibody, or antigen-binding portion thereof, wherein, when administered subcutaneously to a subject at a dose of about 0.3 mg/kg, the antibody, or antigen-binding portion thereof, is capable of exhibiting: (a) an area under the curve (AUC) of between about 125 and about 800 µgh/ml; and (b) a peak concentration ($C_{max}$) of between about 1.0 and about 6.0 µg/ml.

In another aspect, the invention provides an isolated composition comprising an anti-IL-13 antibody, or antigen-binding portion thereof, wherein, when administered subcutaneously to a subject at a dose of about 3 mg/kg, the antibody, or antigen-binding portion thereof, is capable of exhibiting: (a) an area under the curve (AUC) of between about 1,100 and about 8,500 µgh/ml; and (b) a peak concentration ($C_{max}$) of between about 12 and about 60 µg/ml.

In one embodiment, the anti-IL-13 antibody, or antigen-binding portion thereof, is 13C5.5, or an antigen-binding portion thereof. In another embodiment, the composition is a pharmaceutical composition.

In another aspect, the invention provides methods of treating or preventing asthma in a subject by administering a composition of the invention to the subject, thereby treating or preventing asthma. In one embodiment, the composition is administered once. In another embodiment, the composition is administered weekly. In yet another embodiment, the composition is administered for about 3 weeks.

In one embodiment, the asthma is mild to moderate asthma. In another embodiment, the subject is a human.

In another embodiment, the method further comprises the administration of an additional agent. In one embodiment, the additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

In another aspect, the invention provides methods of treating asthma in a subject by intravenously administering to the subject an anti-IL-13 antibody, or antigen-binding portion thereof, wherein at least one pharmacokinetic characteristic selected from the group consisting of: (a) a maximum serum concentration ($C_{max}$) of between about 5 and about 235 µg/mL, and (b) an area under the serum concentration-time curve (AUC) of between about 1,500 and about 98,000 µgh/mL, is achieved following administration of the antibody, or antigen-binding portion thereof to the subject.

In one embodiment, the antibody, or antigen-binding portion thereof, is administered at a dose of about 0.3 mg/kg. In one embodiment, the $C_{max}$ is between about 5 and about 10 µg/mL. In one embodiment, the AUC is between about 1,500 and about 2,700 µgh/mL.

In another embodiment, the antibody, or antigen-binding portion thereof, is administered at a dose of about 3 mg/kg. In one embodiment, the $C_{max}$ is between about 55 and about 90 µg/mL. In another embodiment, the AUC is between about 20,000 and about 34,000 µgh/mL.

In another embodiment, the antibody, or antigen-binding portion thereof, is administered at a dose of about 10 mg/kg. In one embodiment, the $C_{max}$ is between about 190 and about 235 µg/mL. In one embodiment, the AUC is between about 75,000 and about 100,000 µgh/mL.

In another embodiment, the $C_{max}$ value is between about 20 and about 30 (µg/mL)/(mg/kg) after dose normalization. In another embodiment, the AUC is between about 6,000 and about 10,000 (µgh/mL)/(mg/kg) after dose normalization.

In another aspect, the invention provides methods of treating asthma in a subject by subcutaneously administering to the subject an anti-IL-13 antibody, or antigen-binding portion thereof, wherein at least one pharmacokinetic characteristic selected from the group consisting of: (a) a maximum serum concentration ($C_{max}$) of between about 1 and about 60 µg/mL, and (b) an area under the serum concentration-time curve (AUC) of between about 125 and about 8,100 µgh/mL, is achieved following administration of the antibody, or antigen-binding portion thereof to the subject.

In one embodiment, the antibody, or antigen-binding portion thereof, is administered at a dose of about 0.3 mg/kg. In one embodiment, the $C_{max}$ is between about 1 and about 6 µg/mL. In another embodiment, the AUC is between about 100 and about 800 µgh/mL.

In another embodiment, the antibody, or antigen-binding portion thereof, is administered at a dose of about 3 mg/kg. In one embodiment, the $C_{max}$ is between about 12 and about 60 µg/mL. In another embodiment, the AUC is between about 1,100 and about 8,100 µgh/mL.

In one embodiment, the anti-IL-13 antibody, or antigen-binding portion thereof, is 13C5.5, or an antigen-binding portion thereof. In another embodiment, the subject is a human. In another embodiment, the anti-IL-13 antibody, or antigen-binding portion thereof, is administered once. In another embodiment, the anti-IL-13 antibody, or antigen-binding portion thereof, is administered weekly. In yet another embodiment, the anti-IL-13 antibody, or antigen-binding portion thereof, is administered for three weeks.

In one embodiment, the asthma is mild to moderate asthma.

In another embodiment, the method further comprises the administration of an additional agent. In one embodiment, the additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

In another aspect, the invention provides methods for treating asthma in a subject by subcutaneously administering to the subject an anti-IL-13 antibody, or antigen-binding portion thereof, at a dose of about 0.3 mg/kg, wherein at least one pharmacokinetic characteristic selected from the group consisting of: (a) a half-life of between about 24 and 31 days; (b) a $T_{max}$ of between about 3 and about 5 days; and (c) a bioavailability of at least about 60% is achieved following administration of the antibody, or antigen-binding portion thereof to the subject. In one embodiment, the bioavailability is at least about 70%.

In another aspect, the invention provides methods of treating asthma in a subject by subcutaneously administering to the subject an anti-IL-13 antibody, or antigen-binding portion thereof, at a dose of about 3 mg/kg, wherein at least one pharmacokinetic characteristic selected from the group consisting of: (a) a half-life of between about 23 and 26 days; (b) a $T_{max}$ of less than or equal to about 5 days; and (c) a bioavailability of at least about 60% is achieved following administration of the antibody, or antigen-binding portion thereof to the subject. In one embodiment, the bioavailability is at least about 70%.

In another aspect, the invention provides methods of treating asthma in a subject comprising intravenously administering to the subject an anti-IL-13 antibody, or antigen-binding portion thereof, at a dose of about 0.3 mg/kg, wherein at least one pharmacokinetic characteristic selected from the group consisting of: (a) a clearance rate of between about 0.11 to about 0.19 mL/hr/kg; and (b) a volume of distribution of between about 70 to about 130 mL/kg is achieved following administration of the antibody, or antigen-binding portion thereof to the subject.

In another aspect, the invention provides methods treating asthma in a subject by intravenously administering to the subject an anti-IL-13 antibody, or antigen-binding portion thereof, at a dose of about 3 mg/kg, wherein at least one pharmacokinetic characteristic selected from the group consisting of: (a) a clearance rate of between about 0.08 to about 0.14 mL/hr/kg; and (b) a volume of distribution of between about 55 to about 100 mL/kg is achieved following administration of the antibody, or antigen-binding portion thereof to the subject.

In another aspect, the invention provides methods of treating asthma in a subject comprising intravenously administering to the subject an anti-IL-13 antibody, or antigen-binding portion thereof, at a dose of about 10 mg/kg, wherein at least one pharmacokinetic characteristic selected from the group consisting of: (a) a clearance rate of between about 0.09 to about 0.13 mL/hr/kg; and (b) a volume of distribution of between about 85 to about 130 mL/kg is achieved following administration of the antibody, or antigen-binding portion thereof to the subject.

In one embodiment, the anti-IL-13 antibody, or antigen-binding portion thereof, is 13C5.5, or an antigen-binding portion thereof. In another embodiment, the subject is a human. In one embodiment, the anti-IL-13 antibody, or antigen-binding portion thereof, is administered once. In another embodiment, the anti-IL-13 antibody, or antigen-binding portion thereof, is administered weekly. In yet another embodiment, the anti-IL-13 antibody, or antigen-binding portion thereof, is administered for 3 weeks.

In one embodiment, the asthma is mild to moderate asthma.

In another embodiment, the methods further comprise the administration of an additional agent. In one embodiment, the additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

In one embodiment, the subject is a human.

In another aspect, the invention provides an isolated composition comprising an anti-IL-13 antibody, or antigen-binding portion thereof, wherein, when administered intravenously to a subject at a dose of about 0.3 mg/kg, 1 mg/kg, 3 mg/kg or 10 mg/kg, the antibody, or antigen-binding portion thereof, is capable of exhibiting any of the pharmacokinetic parameters set forth in the specification, Tables or Figures.

In another aspect, the invention provides an isolated composition comprising an anti-IL-13 antibody, or antigen-binding portion thereof, wherein, when administered subcutaneously to a subject at a dose of about 0.3 mg/kg, 1 mg/kg or 3 mg/kg, the antibody, or antigen-binding portion thereof, is capable of exhibiting any of the pharmacokinetic parameters set forth in the specification, Tables or Figures.

In another aspect, the invention provides methods of treating or preventing asthma in a subject by intravenously administering to the subject an anti-IL-13 antibody, or antigen-binding portion thereof, at a dose of about 0.3 mg/kg, 1 mg/kg, 3 mg/kg or 10 mg/kg, wherein at least one of the pharmacokinetic characteristics set forth in the specification, Tables or Figures is achieved following administration of the antibody, or antigen-binding portion thereof, to the subject.

In yet another aspect, the invention provides methods of treating or preventing asthma in a subject by subcutaneously administering to the subject an anti-IL-13 antibody, or antigen-binding portion thereof, at a dose of about 0.3 mg/kg, 1 mg/kg, 3 mg/kg or 10 mg/kg, wherein at least one of the pharmacokinetic characteristics set forth in the specification, Tables or Figures is achieved following administration of the antibody, or antigen-binding portion thereof, to the subject.

BRIEF DESCRIPTION OF THE DRAWINGS

FIG. 1 is a graph depicting that IL-13 expression precedes pulmonary dysfunction.

FIG. 2 depicts that 13C5.5, an anti-IL-13 antibody, is derived from a hybridoma with a unique epitope and lineage.

FIG. 3 depicts that 13C5.5, an anti-IL-13 antibody, neutralizes IL-13 in the lung.

FIG. 4 depicts the schematic of first in human (FIH) dosing used in the Phase I Clinical Trial.

FIG. 5 depicts the mean 13C5.5 serum concentration-time profile after single 0.3 mg/kg, 1 mg/kg, 3 mg/kg, and 10 mg/kg intravenous infusions of 13C5.5 to healthy subjects on a linear scale.

FIG. 6 depicts the pharmacokinetic parameters of 13C5.5, an anti-IL-13 antibody.

FIG. 7 depicts the mean 13C5.5 serum concentration-time profile after single 0.3 mg/kg, 1 mg/kg, 3 mg/kg and 10 mg/kg intravenous infusions of 13C5.5 to healthy and asthma subjects on a linear scale.

FIG. 8 depicts the pharmacokinetic parameters of 13C5.5, an anti-IL-13 antibody.

FIG. 9 depicts the pharmacokinetic parameters of 13C5.5, an anti-IL-13 antibody.

FIG. 10 depicts the pharmacokinetic parameters of 13C5.5, an anti-IL-13 antibody. Bioavailability following subcutaneous administration was estimated to be about 70%.

FIG. 11 depicts the mean dose normalized Cmax values following three weekly 0.3 mg/kg (Group 8) and 3 mg/kg (Group 9) subcutaneous injections of 13C5.5 (Part 3 of the Clinical Trial).

FIG. 12 depicts the mean dose normalized $AUC_{0-168}$ values following three weekly 0.3 mg/kg (Group 8) and 3 mg/kg (Group 9) subcutaneous injections of 13C5.5 (Part 3 of the Clinical Trial).

DETAILED DESCRIPTION OF THE INVENTION

The present invention provides methods and compositions for treating asthma, e.g., mild or moderate asthma, using an anti-IL-13 antibody, or antigen-binding portion thereof.

In order that the present invention may be more readily understood, certain terms are first defined.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "IL-13" and "IL-13 wild type" (abbreviated herein as IL-13, IL-13 wt), as used herein, include a cytokine that is secreted primarily by T helper 2 cells. The term includes a monomeric protein of 13 kDa polypeptide. The structure of IL-13 is described further in, for example, Moy, Diblasio et al. 2001 J Mol Biol 310 219-30. The term IL-13 is intended to include recombinant human IL-13 (rh IL-13), which can be prepared by standard recombinant expression methods. The amino acid sequence of human IL-13, SEQ ID NO. 1, is known in the art.

Sequence of human IL-13-
SEQ ID NO: 1
MALLLTTVIALTCLGGFASPGPVPPSTALRELIEELVNITQNQKAPLCNG
SMVWSINLTAGMYCAALESLINVSGCSAIEKTQRMLSGFCPHKVSAGQFS
SLHVRDTKIEVAQFVKDLLLHLKKLFREGRFN The term "IL-13 variant" (abbreviated herein as IL-13v), as used herein, includes a variant of IL-13 wherein amino acid residue 130 of SEQ ID NO:1 is changed from Arginine to Glutamine (R130Q).

"Biological activity" as used herein, refers to all inherent biological properties of the cytokine. Biological properties of IL-13 include but are not limited to binding IL-13 receptor; (other examples include immunoglobulin isotype switching to IgE in human B cells and suppressing inflammatory cytokine production).

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed herein. In one embodiment, the antibody used in the compositions and methods of the invention is the anti-IL-13 antibody 13C5.5 described in U.S. Pat. No. 7,915,388, incorporated by reference herein. In another embodiment, the antibody used in the compositions and methods of the invention is the antibody 6A1, 3G4, tralokinumab, lebrikizumab, QAZ-576, IMA-638 or IMA-026.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., IL-13). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art and disclosed in Table 2 of U.S. Pat. No. 7,915,388, the entire contents of which are incorporated herein by reference.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds IL-13 is substantially free of antibodies that specifically bind antigens other than IL-13). An isolated antibody that specifically binds IL-13 may, however, have cross-reactivity to other antigens, such as IL-13 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in U.S. Pat. No. 7,915,388, the contents of which are incorporated herein by reference), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human IL-13 which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti human IL-13 antibodies and antigen binding portions are provided. Such antibodies were generated by obtaining murine anti-IL-13 monoclonal antibodies using traditional hybridoma technology followed by humanization using in vitro genetic engineering, such as those disclosed in Kasaian et al PCT publication No. WO 2005/123126 A2.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 96%, at least 97%, at least 98%, at least 99%, or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4 disclosed in U.S. Pat. No. 7,915,388, the contents of which are incorporated herein by reference.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 96%, at least 97%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CHL hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

In one embodiment of the invention, the humanized anti-IL-13 antibody is 13C5.5. 13C5.5 has the sequences SEQ ID NO:2 (heavy chain variable region) and SEQ ID NO:3 (light chain variable region). See also U.S. Pat. No. 7,915,388, the entire contents of which are incorporated herein by reference.

```
Heavy Chain Variable Region 13C5.5
                                       SEQ ID NO: 2
EVTLRESGPGLVKPTQTLTLTCTLYGFSLSTSDMGVDWIRQPPGKGLEWL
AHIWWDDVKRYNPALKSRLTISKDTSKNQVVLKLTSVDPVDTATYYCART
VSSGYIYYAMDYWGQGTLVTVSS Light Chain Variable Region 13C5.5
                                       SEQ ID NO: 3
DIQMTQSPSSLSASVGDRVTISCRASQDIRNYLNWYQQKPGKAPKLLIFY
TSKLHSGVPSRFSGSGSGTDYTLTISSLQPEDIATYYCQQGNTLPLTFGG
GTKVEIK
```

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e. capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of a cytokine when a binding protein specifically binds the cytokine. Preferably a neutralizing binding protein is a neutralizing antibody whose binding to IL-13 and/or IL-13 results in inhibition of a biological activity of IL-13 and/or IL-13. Preferably the neutralizing binding protein binds IL-13 and/or IL-13 and reduces a biologically activity of IL-13 and/or IL-13 by at least about 20%, 40%, 60%, 80%, 85% or more. Inhibition of a biological activity of IL-13 and/or IL-13 by a neutralizing binding protein can be assessed by measuring one or more indicators of IL-13 and/or IL-13 biological activity well known in the art. For example, inhibition of human IL-13 induced production of TARC (CCL-17) by A-549 cells can be measured (see Example 1.1.0 of U.S. Pat. No. 7,915,388, the contents of which are incorporated herein by reference).

The term "activity" includes activities such as the binding specificity/affinity of an antibody for an antigen, for example, an anti-IL-13 antibody that binds to an IL-13 antigen and/or the neutralizing potency of an antibody, for example, an anti-IL-13 antibody whose binding to IL-13 inhibits the biological activity of IL-13, e.g. For example inhibition of human IL-13 induced production of TARC (CCL-17) by A-549 cells (see Example 1.1.0 of U.S. Pat. No. 7,915,388, the entire contents of which are incorporated herein by reference).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., 3H, 14C, 35S, 90Y, 99Tc, 111In, 125I, 131I, 177Lu, 166Ho, or 153Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism;

in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162, the entire contents of which are incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of IL-13). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of IL-13). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-13 polypeptides or polypeptides, nucleic acids, carbohydrates, or any other molecules that bind to IL-13.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of IL-13 and/or IL-13. Antagonists and inhibitors of IL-13 and/or IL-13 may include, but are not limited to, proteins; nucleic acids, carbohydrates, or any other molecules, which bind to IL-13 and/or IL-13.

The term "inhibit binding to the receptor" refers to the ability of the binding protein to prevent the binding of IL-13 to one or more of its receptors. Such inhibition of binding to the receptor would result in diminishing or abolishing the biological activity mediated by binding of IL-13 to its receptor or receptors.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

The term "$C_{max}$" refers to the maximum or peak serum or plasma concentration of an agent observed in a subject after its administration.

In one embodiment, the anti-IL-13 antibody, or antigen-binding portion thereof, of the invention (e.g., a humanized anti-IL-13 antibody such as 13C5.5, or an antigen-binding portion thereof) is administered intravenously and exhibits a maximum serum concentration ($C_{max}$) of between about 5 and about 235 µg/mL; a peak concentration ($C_{max}$) of between about 5 and about 8 µg/ml; a $C_{max}$ of between about 5 and about 10 µg/mL; a peak concentration ($C_{max}$) of between about 55 and about 90 µg/ml; a peak concentration ($C_{max}$) of between about 185 and about 250 µg/ml; a $C_{max}$ of between about 190 and about 235 µg/mL. In another embodiment, the $C_{max}$ is between about 5 and about 50, between about 50 and about 75, between about 75 and about 100, between about 100 and about 125, between about 125 and about 150, between about 150 and about 175, between about 175 and about 200, or between about 200 and about 235 µg/mL.

In another embodiment, the anti-IL-13 antibody, or antigen-binding portion thereof (e.g., a humanized anti-IL-13 antibody such as 13C5.5, or an antigen-binding portion thereof), is administered intravenously and exhibits a $C_{max}$ value of between about 20 and about 30 (µg/mL)/(mg/kg) after dose normalization. In another embodiment, the anti-IL-13 antibody, or antigen-binding portion thereof, is administered intravenously and exhibits a $C_{max}$ value of about 20, about 21, about 22, about 23, about 24, about 25, about 26, about 27, about 28, about 29 and about 30 (µg/mL)/(mg/kg) after dose normalization. In another embodiment, the anti-IL-13 antibody, or antigen-binding portion thereof, is administered intravenously and exhibits a $C_{max}$ value of between about 10 and about 40 (µg/mL)/(mg/kg) after dose normalization.

In another embodiment, the anti-IL-13 antibody, or antigen-binding portion thereof, of the invention (e.g., a humanized anti-IL-13 antibody such as 13C5.5, or an antigen-binding portion thereof) is administered subcutaneously and exhibits a maximum serum concentration ($C_{max}$) of between about 1 and about 60 µg/mL; a peak concentration ($C_{max}$) of between about 1.0 and about 6.0 µg/ml; a $C_{max}$ value of between about 6 and about 12 µg/ml; a peak concentration ($C_{max}$) of between about 12 and about 60 µg/ml; a $C_{max}$ value of between about 1 and about 10, between about 10 and about 20, between about 20 and about 30, between about 30 and about 40, between about 40 and about 50, between about 50 and about 60, between about 20 and about 60, or between about 40 and about 60 µg/ml.

The term "$T_{max}$" refers to the time at which $C_{max}$ occurred. In one embodiment, the anti-IL-13 antibody, or antigen-binding portion thereof, of the invention (e.g., a humanized anti-IL-13 antibody such as 13C5.5, or an antigen-binding portion thereof) is administered intravenously or subcutaneously and exhibits a $T_{max}$ of between about 1 and about 5 days; a $T_{max}$ of between about 3 and about 5 days; a $T_{max}$ of less than or equal to about 5 days; a $T_{AX}$ of about 1 day, a $T_{AX}$ of about 2 days, a $T_{AX}$ of about 3 days, a $T_{max}$ of about 4 days, a $T_{max}$ of about 5 days, a $T_{max}$ of about 6 days, a $T_{max}$ of about 7 days, a $T_{max}$ of about 8 days, a $T_{max}$ of about 9 days, or a $T_{AX}$ of about 10 days.

The term "bioavailability" or "F %" refers to a fraction or percent of a dose which is absorbed and enters the systemic circulation after administration of a given dosage form. The dose of the anti-IL-13 antibody, or antigen-binding portion thereof, may be administered through any route, and, preferably, via intravenous or subcutaneous injection. In one embodiment, the anti-IL-13 antibody, or antigen-binding portion thereof, of the invention (e.g., a humanized anti-IL-13 antibody such as 13C5.5, or an antigen-binding portion thereof) is administered intravenously or subcutaneously and exhibits a bioavailability of at least about 60%. In another embodiment, the antibody, or antigen-binding portion thereof, exhibits a bioavailability of at least about 35%, at least about 40%, at least about 45%, at least about 50%, at least about 60%, at least about 65%, at least about 70%, at least about 75%, at least about 80%, at least about 85%, at least about 90%, at least about 95%, or at least about 100%.

The term "AUC" or "area under the curve" is related to clearance. A higher clearance rate is related to a smaller AUC, and a lower clearance rate is related to a larger AUC value. The AUC higher values represent slower clearance rates.

In one embodiment, the anti-IL-13 antibody, or antigen-binding portion thereof, of the invention (e.g., a humanized anti-IL-13 antibody such as 13C5.5, or an antigen-binding portion thereof) is administered intravenously and exhibits an area under the curve (AUC) of between about 75 and about 100,000 µgh/mL; an AUC of between about 75 and about 100; between about 1,500 and about 2,700 µgh/ml; between about 1,500 and about 3,000; between about 21,000 and about 33,500 µgh/ml; between about 1,500 and 98,000; between about 20,000 and about 34,000 µgh/mL; between about 34,000 and about 40,000; between about 40,000 and about 50,000; between about 50,000 and about 60,000; between about 60,000 and about 75,000; between about 75,000 and about 100,000 µgh/mL; about 75, about 100, about 150, about 200, about 250, about 300, about 350, about 400, about 450, about 500, about 550, about 600, about 650, about 700, about 750, about 800, about 850, about 900, about 950, about 1,000; about 1,100; about 1,200; about 1,300; about 1,400; about 1,500; about 1,600; about 1,700; about 1,800; about 1,900; about 2,000; about 2,250; about 2,500; about 2,750; about 3,000; about 4,000; about 5,000; about 6,000; about 7,000; about 8,000; about 9,000; about 10,000; about 12,000; about 15,000; about 20,000; about 25,000; about 30,000; about 35,000; about 40,000; about 45,000; about 50,000; about 55,000; about 60,000; about 65,000; about 70,000; about 75,000; about 80,000; about 85,000; about 90,000; about 95,000 or about 100,000 µgh/mL.

In another embodiment, the AUC is between about 6,000 and about 10,000 (µgh/mL)/(mg/kg) after dose normalization, between about 7,000 and about 9,000; about 6,000; about 6,500; about 7,000; about 7,500; about 8,000; about 8,500; about 9,000; about 9,500 or about 10,000 (µgh/mL)/(mg/kg) after dose normalization.

In another embodiment, the anti-IL-13 antibody, or antigen-binding portion thereof, of the invention (e.g., a humanized anti-IL-13 antibody such as 13C5.5, or an antigen-binding portion thereof) is administered subcutaneously and exhibits an area under the curve (AUC) of between about 125 and about 8,100 µgh/mL; between about 125 and about 800 µgh/ml; between about 800 and about 1,100; between about 1,100 and about 8,100; about 100 and about 800 µgh/mL; about 125; about 150; about 175; about 200; about 250; about 300; about 350; about 400; about 450; about 500; about 550; about 600; about 650; about 700; about 750; about 800; about 850; about 900; about 950; about 1,000; about 1,100; about 1,200; about 1,300; about 1,400; about 1,500; about 1,600; about 1,700; about 1,800; about 1,900; about 2,000; about 2,250; about 2,500; about 3,000; about 3,500; about 4,000; about 4,500; about 5,000; about 5,500; about 6,000; about 6,500; about 7,000; about 7,500; about 8,000 or about 8,100 µgh/mL.

As used herein, the term "clearance rate" is related to the AUC, or area under the curve. A higher clearance rate is related to a smaller AUC, and a lower clearance rate is related to a larger AUC value. The AUC higher values represent slower clearance rates.

In one embodiment, the anti-IL-13 antibody, or antigen-binding portion thereof, of the invention (e.g., a humanized anti-IL-13 antibody such as 13C5.5, or an antigen-binding portion thereof) is administered intravenously and exhibits a clearance rate of between about 0.08 and about 0.2 ml/h/kg, between about 0.08 and about 0.15 ml/h/kg; between about 0.1 and about 0.15 ml/h/kg; between about 0.11 to about 0.19 mL/hr/kg; between about 0.08 to about 0.14 mL/hr/kg; between about 0.09 to about 0.13 mL/hr/kg; about 0.08; about 0.09, about 0.1, about 0.11, about 0.12, about 0.13, about 0.14, about 0.15, about 0.16, about 0.17, about 0.18, about 0.19, about 2.0, about 2.1, about 2.2, about 2.3, about 2.4 or about 2.5 mL/h/kg.

As used herein, the term "volume of distribution" is a term used to quantify the distribution of a drug, e.g., an anti-IL-13 antibody, or antigen-binding portion thereof, between plasma and the rest of the body after dosing. The volume of distribution is the theoretical volume in which the total amount of drug would need to be uniformly distributed in order to produced the desired blood concentration of the drug.

In one embodiment, the anti-IL-13 antibody, or antigen-binding portion thereof, of the invention (e.g., a humanized anti-IL-13 antibody such as 13C5.5, or an antigen-binding portion thereof) is administered intravenously and exhibits a volume of distribution of between about 55 and about 130 mL/kg; between about 65 and 125 mL/kg; between about 55 and about 100 mL/kg; between about 90 and about 130 mL/kg; between about 70 to about 130 mL/kg; between about 85 to about 130 mL/kg; between about 100 to about 130; between about 110 to about 120; about 55, about 60, about 65, about 70, about 75, about 80, about 85, about 90, about 95, about 100, about 105, about 110, about 115, about 120, about 125, about 130 or about 135 mL/kg.

In one embodiment, the anti-IL-13 antibody, or antigen-binding portion thereof, of the invention (e.g., a humanized anti-IL-13 antibody such as 13C5.5, or an antigen-binding portion thereof) is administered intravenously or subcutaneously and has a half-life of between about 24 and 31 days; between about 23 and 26 days; between about 10 and about 40 days, between about 20 and about 30 days, about 10 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, or about 40 days.

The term "dosing" or "dose" or "dosage", as used herein, refers to the administration of a substance (e.g., an anti-IL-13 antibody, or antigen-binding portion thereof) to achieve a therapeutic objective (e.g., the treatment of asthma).

In one embodiment, the composition of the invention is administered once. In another embodiment, the composition of the invention is administered weekly. In another embodiment, the composition of the invention is administered for two weeks. In another embodiment, the composition of the invention is administered for three weeks. In another embodiment, the composition is administered for four weeks, five weeks, six weeks, seven weeks, eight weeks, nine weeks, ten weeks, eleven weeks, three months, four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months, two years, three years, four years, five years, ten years, or for the life of the subject.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-IL-13 antibody and another drug. The other drug(s) may be administered concomitant with, prior to, or following the administration of the anti-IL-13 antibody.

The term "kit" as used herein refers to a packaged product comprising components with which to administer the anti-IL-13 antibody of the invention for treatment of a IL-13 related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering an anti-IL-13 antibody.

Various aspects of the invention are described in further detail in the following subsections.

I. Antibodies that Bind IL-13

This invention provides methods and compositions for using anti-IL-13 antibodies, or antigen-binding portions thereof, for the treatment of asthma. In one aspect, the present invention provides compositions which include and/or methods which use isolated murine monoclonal antibodies, or antigen-binding portions thereof, that bind to IL-13 with high affinity, a slow off rate and high neutralizing capacity. In a second aspect, the invention provides compositions which include and/or methods which use chimeric antibodies that bind IL-13. In a third aspect, the invention provides compositions which include and/or methods which use humanized antibodies, or antigen-binding portions thereof, that bind IL-13. Preferably, the antibodies, or portions thereof, are isolated antibodies. Preferably, the antibodies are neutralizing anti-IL-13 and/or humanized or human anti-IL-13 antibodies.

A. Methods of Making Anti-IL-13 Antibodies

Antibodies to be used in the compositions and/or methods of the present invention may be made by any of a number of techniques known in the art. For example, they can be made using the techniques disclosed in U.S. Pat. No. 7,915,338, the entire contents of which are incorporated herein by reference.

1. Anti-IL-13 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1.2). Briefly, mice can be immunized with an IL-13 antigen. In a preferred embodiment, the IL-13 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with an IL-13 antigen, antibodies and/or antibody-producing cells may be obtained from the animal. An anti-IL-13 antibody-containing serum is obtained from the animal by bleeding or sacrificing the animal. The serum may be used as it is obtained from the animal, an immunoglobulin fraction may be obtained from the serum, or the anti-IL-13 antibodies may be purified from the serum. Serum or immunoglobulins obtained in this manner are polyclonal, thus having a heterogeneous array of properties.

Once an immune response is detected, e.g., antibodies specific for the antigen IL-13 are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding IL-13. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IL-13, or a portion thereof, or a cell expressing IL-13. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-IL-13 antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IL-13 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-IL-13 Monoclonal Antibodies Using SLAM

Recombinant antibodies for use in the compositions and/or methods of the present invention may also be generated from single, isolated lymphocytes using a procedure referred to in the art as the selected lymphocyte antibody method (SLAM), as described in U.S. Pat. Nos. 7,915,388 and 5,627,052, PCT Publication WO 92/02551 and Babcock, J. S. et al. (1996) Proc. Natl. Acad. Sci. USA 93:7843-7848, the entire contents of each of which are incorporated herein by reference. Briefly, single cells secreting antibodies of interest, e.g., lymphocytes derived from any one of the immunized animals described above, are screened using an antigen-specific hemolytic plaque assay, wherein the antigen IL-13, a subunit of IL-13, or a fragment thereof, is coupled to sheep red blood cells using a linker, such as biotin, and used to identify single cells that secrete antibodies with specificity for IL-13. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-13. The amplified immunoglobulin sequences further can be manipulated in vitro, such as by in vitro affinity maturation methods such as those described in PCT Publication WO 97/29131 and PCT Publication WO 00/56772.

3. Anti-IL-13 Monoclonal Antibodies Using Transgenic Animals

Antibodies for use in the compositions and/or methods of the present invention may also be produced by immunizing a non-human animal comprising some, or all, of the human immunoglobulin locus with an IL-13 antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. Nature Genetics 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000, the entire contents of each of which are expressly incorporated herein by reference. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., Nature Genetics 15:146-156 (1997), Green and Jakobovits J. Exp. Med. 188:483-495 (1998), the disclosures of which are hereby incorporated by reference.

4. Anti-IL-13 Monoclonal Antibodies Using Recombinant Antibody Libraries

In vitro methods also can be used to make the antibodies for use in the compositions and/or methods of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, US patent application publication 20030186374, and PCT Publication No. WO 97/29131, the contents of each of which are incorporated herein by reference.

The recombinant antibody library may be from a subject immunized with IL-13 or IL-13, or a portion of IL-13 or IL-13. Alternatively, the recombinant antibody library may be from a naive subject, i.e., one who has not been immunized with IL-13, such as a human antibody library from a human subject who has not been immunized with human IL-13. Antibodies of the invention are selected by screening the recombinant antibody library with the peptide comprising human IL-13 to thereby select those antibodies that recognize IL-13. Methods for conducting such screening and selection are well known in the art, such as described in the references in the preceding paragraph. To select antibodies of the invention having particular binding affinities for IL-13, such as those that dissociate from human IL-13 with a particular k.sub.off rate constant, the art-known method of surface plasmon resonance can be used to select antibodies having the desired k.sub.off rate constant. To select antibodies of the invention having a particular neutralizing activity for IL-13, such as those with a particular an IC.sub.50, standard methods known in the art for assessing the inhibition of IL-13 activity may be used.

In one aspect, the invention pertains to an isolated antibody, or an antigen-binding portion thereof, that binds human IL-13. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies for use in the compositions and/or methods of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

B. Production of Recombinant IL-13 Antibodies

Antibodies for use in the compositions and/or methods of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti IL-13 Antibodies

Table 5 of U.S. Pat. No. 7,195,388 (the contents of which are incorporated herein by reference) is a list of amino acid sequences of VH and VL regions of preferred anti-IL-13 antibodies to be used in the compositions and/or methods of the invention. These isolated anti-IL-13 antibody CDR sequences establish a family of IL-13 binding proteins, isolated in accordance with this invention, and comprising polypeptides that include the CDR sequences listed in Table 6 of U.S. Pat. No. 7,195,388 (the contents of which are incorporated herein by reference). To generate and to select CDRs of the invention having preferred IL-13 binding and/or neutralizing activity with respect to IL-13 and/or IL-13, standard methods known in the art for generating binding proteins of the present invention and assessing the IL-13 and or IL-13 binding and/or neutralizing characteristics of those binding protein may be used, including but not limited to those specifically described herein.

In one embodiment, the antibody used in the compositions and/or methods of the invention is the antibody 13C5.5 (see U.S. Pat. No. 7,915,388, the entire contents of which are incorporated herein by reference). 13C5.5 is a humanized antibody that binds with great affinity to helices A and D of interleukin 13 (IL-13) (see FIG. 1). The heavy and light chain variable region sequences of 13C5.5 are set forth above as SEQ ID NO:2 and SEQ ID NO:3, respectively.

2. Anti IL-13 Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail in Example 2.1. See e.g., Morrison, Science 229:1202 (1985); Oi et al., BioTechniques 4:214 (1986); Gillies et al., (1989) J. Immunol. Methods 125:191-202; U.S. Pat. Nos. 5,807, 715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies for use in the compositions and/or methods of the invention are produced by replacing the heavy chain constant region of the murine monoclonal anti human IL-13 antibodies described in section 1 with a human IgG1 constant region. In a specific embodiment the chimeric antibody of the invention comprises a heavy chain variable region (VH) comprising the amino acid sequence of SEQ ID NO: 34; SEQ ID NO: 36; SEQ ID NO: 41; SEQ ID NO: 42; SEQ ID NO: 46 and a light chain variable region (VL) comprising the amino acid sequence of SEQ ID NO: 35; SEQ ID NO: 37; SEQ ID NO: 40; SEQ ID NO: 43; or SEQ ID NO: 47 disclosed in U.S. Pat. No. 7,195,388.

3. Anti IL-13 Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., Kabat et al., Sequences of Proteins of Immunological Interest, U.S. Dept. Health (1983), entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994), Roguska. et al., PNAS 91:969-973 (1994); PCT publication WO 91/09967, PCT/: US98/16280, US96/ 18978, US91/09630, US91/05939, US94/01234, GB89/ 01334, GB91/01134, GB92/01755; WO90/14443, WO90/ 14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

C. Production of Antibodies and Antibody-Producing Cell Lines

Preferably, anti-IL-13 antibodies for use in the compositions and/or methods of the present invention exhibit a high capacity to reduce or to neutralize IL-13 activity, e.g., as assessed by any one of several in vitro and in vivo assays known in the art (e.g., see Example 1.1.0 of U.S. Pat. No. 7,195,388, the entire contents of which are incorporated herein by reference.). For example, these antibodies neutralize IL-13-induced production of TARC by A-549 cells with $IC_{50}$ values in the range of at least about $10^{-8}$M, about $10^{-9}$ M, or about $10^{-10}$ M.

In preferred embodiments, the isolated antibody, or antigen-binding portion thereof, binds human IL-13, wherein the antibody, or antigen-binding portion thereof, dissociates from human IL-13 with a $k_{off}$ rate constant of about 0.1 s$^{-1}$ or less, as determined by surface plasmon resonance, or which inhibits human IL-13 and/or human IL-13 activity with an IC$_{50}$ of about 1×10.sup.-6M or less. Alternatively, the antibody, or an antigen-binding portion thereof, may dissociate from human IL-13 with a $k_{off}$ rate constant of about 1×10$^{-2}$ s$^{-1}$ or less, as determined by surface plasmon resonance, or may inhibit human IL-13 and/or human IL-13 activity with an IC$_{50}$ of about 1×10$^{-7}$M or less. Alternatively, the antibody, or an antigen-binding portion thereof, may dissociate from human IL-13 with a $k_{off}$ rate constant of about 1×10$^{-3}$ s$^{-1}$ or less, as determined by surface plasmon resonance, or may inhibit human IL-13 and/or human IL-13 with an IC$_{50}$ of about 1×10$^{-8}$M or less. Alternatively, the antibody, or an antigen-binding portion thereof, may dissociate from human IL-13 with a $k_{off}$ rate constant of about 1×10$^{-4}$ s$^{-1}$ or less, as determined by surface plasmon resonance, or may inhibit IL-13 and/or human L-13 activity with an IC$_{50}$ of about 1×10$^{-9}$M or less. Alternatively, the antibody, or an antigen-binding portion thereof, may dissociate from human IL-13 with a $k_{off}$ rate constant of about 1×10$^{-5}$ s$^{-1}$ or less, as determined by surface plasmon resonance, or may inhibit IL-13 and/or human IL-13 activity with an IC$_{50}$ of about 1×10$^{-10}$ M or less. Alternatively, the antibody, or an antigen-binding portion thereof, may dissociate from human IL-13 with a $k_{off}$ rate constant of about 1×10$^{-5}$ s$^{-1}$ or less, as determined by surface plasmon resonance, or may inhibit IL-13 and/or human IL-13 activity with an IC$_{50}$ of about 1×10$^{11}$M or less.

IL-13 exerts its actions by binding to the IL-13 receptor (IL-13R) on the cell surface, the heterodimer comprised of the IL-13Rα1 chain (IL-13Rα1) and the IL-4R chain (IL-4R). IL-13 binds to IL-13Rα1 first with low affinity (KD=2-10 nM) and then recruits IL-4R to the complex, generating a high affinity receptor (KD=0.03-0.4 nM) (Aman, M. J., et al. 1996 J. Biol. Chem. 271, 29265-29270; Miloux, et al. 1997 FEBS Lett. 401, 163-166; Andrews, et al 2002 J. Biol. Chem. 277, 46073-46078). Heterodimerization of IL-13R causes activation of Janus kinases, TYK2 and JAK1, constitutively associated with IL-13Rα1 and IL-4R, respectively, followed by activation of the signal transducer and activator of transcription 6 (STAT6) (Izuhara, K., and Arima, K. 2004 Drug News Perspect. 17, 91-98). There is another IL-13-binding unit, the IL-13Rα2 chain (IL-13Rα2), which binds to IL-13 with high affinity (0.25-1.2 nM) (Caput, et al 1996J. Biol. Chem. 271, 16921-16926; Donaldson et al 1998 J. Immunol. 161, 2317-2324). No other receptor molecule is known to be involved in the IL-131L-13R2 complex. IL-13R2 is initially thought to act as a nonsignaling "decoy" receptor. However, it was later discovered that it can bind to IL-13 and signals through AP-1 pathway, leading to TNF-beta production in certain cell types including macrophages, which in turn leads to lung fibrosis (Fichtner-Feigl, 2006 Nat Med 12:99-106). Therefore both IL-13Rα1/IL-4Rα and IL-13Rα2 pathways contribute to the overall pathophysiology of asthma and other pulmonary inflammatory conditions. Therefore, a therapeutic anti-IL-13 antibody that blocks IL-13 binding to both receptors will be more effective that those that blocks only one receptor.

In one aspect, the instant invention provides compositions and/or methods which use monoclonal antibodies that block IL-13 binding to both IL-13Rα1 and IL-13Rα2. Both ELISA-based receptor binding assay and 125-I-labeled IL-13 binding assay on cell surface demonstrated that 13C5, both murine version and humanized version (i.e., 13C5.5), were able to effective block IL-13 binding to both receptors. Antibodies in the same lineage as 13C5, including 25C8 and 33C3, were also able to block IL-13 binding to both receptors. Epitope mapping of 13C5 indicated that its binding site(s) included the C-terminal Helix D region of human IL-13 (residues VRDTK IEVAQ FVKDL LLHLK KLFRE GR, corresponding to amino acid 104-130 of SEQ ID NO. 1). The c-terminal helix D region has been proposed to be involved in interactions with the IL-13 receptor (Zuegg et al 2001 Immunol Cell Biol. 79:332-9). Crystal structure of human IL-13 complexed with the Fab portion of 13C5.5 antibody indicated that 13C5.5 binds the C-terminal Helix D region as well as the N-terminal Helix A region of human IL-13. Preferably the antibody, or antigen binding fragment thereof binds human IL-13 such that IL-13 with said antibody, or antigen binding fragment thereof, bound to the epitope defined by the topographic regions Ser26-Thr27-Ala28-Leu29-Arg30-Glu31-Leu32-Ile33-Glu34-Glu35-Leu36-Val37-Asn38 and Lys123-Lys124-Leu125-Phe126-Arg127-Glu-128-Gly129-Arg130 of SEQ ID No. 1 is inhibited from binding to the IL-13 receptor. Preferably the antibody, or antigen binding fragment thereof binds human IL-13 such that IL-13 with said antibody, or antigen binding fragment thereof, bound to the epitope defined by the topographic regions Arg30-Glu3'-Leu32-Ile33-Glu34-Glu35-Leu36-Val37-Asn38 and Lys123-Lys124-Leu125-Phe126-Arg127 of SEQ ID No. 1 is inhibited from binding to the IL-13.alpha.2 receptor.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

In one embodiment, the methods and compositions of the invention use a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

In another embodiment, the compositions and methods of the invention use a crystallized binding protein. Preferably the invention relates to crystals of whole anti-IL-13 antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636, incorporated herein by reference.

In yet another embodiment, the compositions and/or methods of the invention use a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, Biotechnol. Frog. 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent applications 20040018590 and 20020137134 and PCT publication WO2005100584 A2, the entire contents of each of which are incorporated by reference herein).

The methods and/or compositions of the present invention may also use an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

II. Compositions of the Invention

The invention also provides compositions, e.g., pharmaceutical compositions, comprising an antibody, or antigen-binding portion thereof, of the invention and a pharmaceutically acceptable carrier. The compositions of the invention comprise an anti-IL-13 antibody, or antigen-binding portion thereof, such that when administered intravenously to a subject at a dose of about 0.3 mg/kg, the antibody, or antigen-binding portion thereof, is capable of exhibiting: (a) an area under the curve (AUC) of between about 1,500 and about 2,700 μgh/ml; (b) a volume of distribution of between about 65 and 125 mL/kg; (c) a peak concentration ($C_{max}$) of between about 5 and about 8 μg/ml; and (d) a clearance rate of between about 0.1 and about 0.2 ml/h/kg.

In another aspect, the invention provides an isolated composition comprising an anti-IL-13 antibody, or antigen-binding portion thereof, such that, when administered intravenously to a subject at a dose of about 3 mg/kg, the antibody, or antigen-binding portion thereof, is capable of exhibiting: (a) an area under the curve (AUC) of between about 21,000 and about 33,500 μgh/ml; (b) a volume of distribution of between about 55 and about 100 mL/kg; (c) a peak concentration ($C_{max}$) of between about 55 and about 90 μg/ml; and (d) a clearance rate of between about 0.08 and about 0.15 ml/h/kg.

In another aspect, the invention provides an isolated composition comprising an anti-IL-13 antibody, or antigen-binding portion thereof, such that, when administered intravenously to a subject at a dose of about 10 mg/kg, the antibody, or antigen-binding portion thereof, is capable of exhibiting: (a) an area under the curve (AUC) of between about 75 and about 100 μgh/ml; (b) a volume of distribution of between about 90 and about 130 mL/kg; (c) a peak concentration ($C_{max}$) of between about 185 and about 250 μg/ml; and (d) a clearance rate of between about 0.1 and about 0.15 ml/h/kg.

In yet another aspect, the invention provides an isolated composition comprising an anti-IL-13 antibody, or antigen-binding portion thereof, such that, when administered subcutaneously to a subject at a dose of about 0.3 mg/kg, the antibody, or antigen-binding portion thereof, is capable of exhibiting: (a) an area under the curve (AUC) of between about 125 and about 800 μgh/ml; and (b) a peak concentration ($C_{max}$) of between about 1.0 and about 6.0 μg/ml.

In another aspect, the invention provides an isolated composition comprising an anti-IL-13 antibody, or antigen-binding portion thereof, such that, when administered subcutaneously to a subject at a dose of about 3 mg/kg, the antibody, or antigen-binding portion thereof, is capable of exhibiting: (a) an area under the curve (AUC) of between about 1,100 and about 8,500 μgh/ml; and (b) a peak concentration ($C_{max}$) of between about 12 and about 60 μg/ml.

In another aspect, the invention provides an isolated composition comprising an anti-IL-13 antibody, or antigen-binding portion thereof, such that, when administered intravenously to a subject at a dose of about 0.3 mg/kg, 1 mg/kg, 3 mg/kg or 10 mg/kg, the antibody, or antigen-binding portion thereof, is capable of exhibiting any of the pharmacokinetic parameters set forth in the specification, Tables or Figures.

In another aspect, the invention provides an isolated composition comprising an anti-IL-13 antibody, or antigen-binding portion thereof, such that, when administered subcutaneously to a subject at a dose of about 0.3 mg/kg, 1 mg/kg or 3 mg/kg, the antibody, or antigen-binding portion thereof, is capable of exhibiting any of the pharmacokinetic parameters set forth in the specification, Tables or Figures.

The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which IL-13 activity is detrimental, such as asthma. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

Typically, a pharmaceutical composition of the invention comprises an anti-IL-13 antibody, or antigen-binding portion thereof, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR™ pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the compositions of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel™), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy &Oncology 39:179-189, Song et al., 1995, "Antibody Mediated Lung Targeting of Long-Circulating Emulsions," PDA Journal of Pharmaceutical Science &Technology 50:372-397, Cleek et al., 1997, "Biodegradable Polymeric Carriers for a bFGF Antibody for Cardiovascular Application," Pro. Intl. Symp. Control. Rel. Bioact. Mater. 24:853-854, and Lam et al., 1997, "Microencapsulation of Recombinant Humanized Monoclonal Antibody for Local Delivery," Proc. Intl. Symp. Control Rel. Bioact. Mater. 24:759-760, each of which is incorporated herein by reference in their entireties.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

For intranasal administration of a composition of the invention, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

For oral administration, compositions of the invention can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The methods of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934, 272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR™ pulmonary drug delivery technology (Alkermes, Inc., Cambridge, Mass.).

The methods of the invention may also comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompasses administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The compositions of the invention may be packaged in a hermetically sealed container such as an ampoule or sachette indicating the quantity of the agent. In one embodiment, the compositions of the invention may be supplied as a dry sterilized lyophilized powder or water free concentrate in a hermetically sealed container and can be reconstituted (e.g., with water or saline) to the appropriate concentration for administration to a subject. Preferably, the compositions of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

Compositions of the invention are preferably suitable for parenteral administration. For example, the compositions of the invention may be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex™ (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The compositions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, the compositions of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-13 activity is detrimental. For example, an anti-IL-13 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an anti-Il-13 antibody, or antigen-binding portion thereof, is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. In one embodiment, a therapeutically or prophylactically effective amount of the antibody, or antigen-binding portion thereof, is 0.3 mg/kg. In another embodiment, a therapeutically or prophylactically effective amount of the antibody, or antigen-binding portion thereof, is 3 mg/kg. In another embodiment, a therapeutically or prophylactically effective amount of the antibody, or antigen-binding portion thereof, is 10 mg/kg. In yet another embodiment, a therapeutically or prophylactically effective amount of the antibody, or antigen-binding portion thereof, is 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.25 mg/kg, 1.5 mg/kg, 1.75 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

III. Methods of the Invention

In another aspect, this application features a method of treating (e.g., curing, suppressing, ameliorating, delaying or preventing the onset of, or preventing recurrence or relapse of) or preventing an IL-13-associated disorder, such as asthma, in a subject. The method includes: administering to the subject an IL-13 binding agent (particularly an antagonist), e.g., an anti-IL-13 antibody or antigen-biding portion thereof as described herein, in an amount sufficient to treat or prevent the IL-13-associated disorder, such as asthma. The IL-13 antagonist, e.g., the anti-IL-13 antibody or antigen-binding portion thereof, can be administered to the subject, alone or in combination with other therapeutic modalities as described herein.

In one embodiment, the subject is a mammal, e.g., a human suffering from one or more IL-13-associated disorders, including, e.g., respiratory disorders (e.g., asthma (e.g., allergic and nonallergic asthma or mild asthma, or moderate asthma), chronic obstructive pulmonary disease (COPD), and other conditions involving airway inflammation, eosinophilia, fibrosis and excess mucus production; atopic disorders (e.g., atopic dermatitis and allergic rhinitis). Accordingly, the disclosure includes the use of an IL-13 binding agent (such as an anti-IL-13 antibody or fragment thereof described herein) for a treatment described herein and the use of an IL-13 binding agent (such as an anti-IL-13 antibody or fragment thereof described herein) for preparing a medicament for a treatment described herein.

Examples of IL-13-associated disorders include, but are not limited to, a disorder chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis.

In other embodiments, this application provides a method of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antagonist, e.g., an IL-13 antibody or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or antigen-binding portion thereof, can be administered to the subject, alone or in combination with other therapeutic modalities as described herein. Preferably, the subject is a mammal, e.g., a human suffering from an IL-13-associated disorder, such as asthma, as described herein.

In another aspect, this application provides a method for detecting the presence of IL-13 in a sample in vitro (e.g., a biological sample, such as serum, plasma, tissue, biopsy). The subject method can be used to diagnose a disorder, e.g., asthma, e.g., mild or moderate asthma. The method includes: (i) contacting the sample or a control sample with the anti-IL-13 antibody or fragment thereof as described herein; and (ii) detecting formation of a complex between the anti-IL-13 antibody or fragment thereof, and the sample or the control sample, wherein a statistically significant change in the formation of the complex in the sample relative to the control sample is indicative of the presence of the IL-13 in the sample.

In yet another aspect, this application provides a method for detecting the presence of IL-13 in vivo (e.g., in vivo imaging in a subject). The subject method can be used to diagnose a disorder, e.g., an IL-13-associated disorder, e.g., asthma, e.g., mild or moderate asthma. The method includes: (i) administering the anti-IL-13 antibody or fragment thereof as described herein to a subject or a control subject under conditions that allow binding of the antibody or fragment to IL-13; and (ii) detecting formation of a complex between the antibody or fragment and IL-13, wherein a statistically significant change in the formation of the complex in the subject relative to the control subject is indicative of the presence of IL-13.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more IL-13 antagonists, e.g., anti-IL-13 antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, as described in more herein.

Examples of preferred additional therapeutic agents that can be coadministered and/or coformulated with one or more IL-13 antagonists, e.g., anti-IL-13 antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4. Yet another preferred combination are other key players of the asthmatic response which may act parallel to, dependent on or in concert with IL-13 function; especially preferred are IL-9 antagonists including IL-9 antibodies. It has been shown that IL-13 and IL-9 have overlapping but distinct functions and a combination of antagonists to both may be most effective. Yet another preferred combination are anti-IL-5 antibodies. Yet other preferred combinations include antagonists of chemokines including MCP-1, MCP-4, eotaxins, RANTES, MDC, CCL-12 and CCL-17 (TARC) and chemokine receptors including CCR2, CCR3, CCR4, and CXCR4. Yet combinations can include antagonists to asthma mediators including acid mammalian chitinase, CRHT2, chymase, S1P1, S1P2, Tyk2, ROCKII, Stat6, p38, NFkB, phosphodiesterase 4 (PDE-4), mast cell trytase, NO, adenosine, IKK2, GATA3, ICAM-1, VCAM-1, and ICOS.

As used herein, the term "a disorder in which IL-13 activity is detrimental" is intended to include diseases and other disorders in which the presence of IL-13 in a subject suffering from the disorder has been shown to be or is suspected of being either responsible for the pathophysiology of the disorder or a factor that contributes to a worsening of the disorder. In one embodiment, the disorder in which IL-13 activity is detrimental is asthma, e.g., mild asthma or moderate asthma. Accordingly, a disorder in which IL-13 activity is detrimental is a disorder in which reduction of IL-13 activity is expected to alleviate the symptoms and/or progression of the disorder. Such disorders may be evidenced, for example, by an increase in the concentration of IL-13 in a biological fluid of a subject suffering from the disorder (e.g., an increase in the concentration of IL-13 in serum, plasma, synovial fluid, etc. of the subject), which can be detected, for example, using an anti-IL-13 antibody as described above. Non-limiting examples of disorders that can be treated with the antibodies of the invention include asthma, e.g., mild or moderate asthma, as well as those disorders discussed in the section below pertaining to pharmaceutical compositions of the antibodies of the invention.

IL-13 has been implicated as having a pivotal role in causing pathological responses associated with asthma. However other mediators of differential immunological pathways are also involved in asthma pathogenesis, and blocking these mediators, in addition to IL-13, may offer additional therapeutic benefit. Thus, binding proteins of the invention may be incorporated into DVD-Ig proteins where in the DVD is capable of binding target pairs including, but not limited to, IL-13 and a pro-inflammatory cytokine, such as tumor necrosis factor-α (TNF-α). TNF-α may amplify the inflammatory response in asthma and may be linked to disease severity (McDonnell, et al., Progress in Respiratory Research (2001), 31(New Drugs for Asthma, Allergy and COPD), 247-250). This suggests that blocking both IL-13 and TNF-α may have beneficial effects, particularly in severe airway disease. In a preferred embodiment the DVD-Ig of the invention binds the targets IL-13 and TNFα and is used for treating asthma.

The present invention is further illustrated by the following examples which should not be construed as limiting in any way. The contents of all cited references, including literature references, issued patents, and published patent applications, as cited throughout this application are hereby expressly incorporated herein by reference. It should further be understood that the contents of all the figures and tables attached hereto, as well as the entire contents of U.S. Pat. No. 7,915,388 are expressly incorporated herein by reference.

EXAMPLES

Introduction to Examples

Asthma is a chronic inflammatory disorder of the airways characterized by wheezing, breathlessness, chest tightness, and cough. Asthma affects approximately 20 million people in the US, and about 75% of asthma patients are adults. Of the adult asthma patients, approximately 60% of asthma patients have mild disease, about 20% have moderate disease and the remaining 20% have severe disease.

Interleukin-13 (IL-13) is thought to be pivotal in the pathogenesis of human asthma, in that elevated levels of IL-13 are present in the lungs of asthma patients, and these levels correlate with disease severity (FIG. 1). Likewise, increased IL-13 is present in both sputum and in lung biopsies of patients with moderate to severe asthma who are treated with inhaled corticosteroids (ICS) or systemic corticosteroids and continue to be symptomatic. Moreover, human IL-13 genetic polymorphisms are associated with asthma and atopy (allergic hypersensitivity). IL-13 binds to two receptors, IL-13Rα1 and IL-13Rα2. IL-13 is a well-validated target for asthma as efficacy has been demonstrated using various means of IL-13 antagonism in multiple, pre-clinical models of asthma.

13C5.5 is a humanized recombinant immunoglobulin IgG1 (IgG1, κ) monoclonal antibody (mAb) specific for human wild-type and variant IL-13. 13C5.5 recognizes a unique epitope on IL-13 that blocks its binding to both IL-13 receptors α1 and α2 (FIG. 2); other similar IL-13-binding antibodies analyzed to date only block the α1 receptor as determined by crystallography and biochemical characterization. 13C5.5 is selective for IL-13, and does not recognize other cytokines. Two residues (L240A and L241A) in the heavy chain were mutated to prevent Fc gamma receptor and complement binding. Likewise, 13C5.5 does not bind or stimulate human whole blood cells to release cytokines. The heavy and light chain variable regions are set forth above as SEQ ID NO:2 and SEQ ID NO:3, respectively.

13C5.5 binds both human wild type and variant IL-13 with high affinity and potency; this is important because variant IL-13 is present in ~20% of human asthmatics. 13C5.5 does not cross-react with mouse, sheep, or dog IL-13. 13C5.5 does cross-react with cynomolgus monkey rIL-13 with a 51 fold lower in vitro potency and with rat rIL-13 with a 155 fold lower in vitro potency compared to human rIL-13. Although the affinity and potency of 13C5.5 is lower against cynomolgus and rat rIL-13 in vitro, 13C5.5 fully neutralizes cynomolgus monkey rIL-13 in vitro with a half maximal inhibitory concentration ($IC_{50}$) of 4.1 nM and rat IL-13 with an $IC_{50}$ of 12.4 nM.

Initial pharmacokinetic analysis following single-dose administration of 13C5.5 was conducted in Sprague-Dawley rats and cynomolgus monkey (FIG. 3). 13C5.5 generally exhibited low clearance, low volume of distribution, and high bioavailability. The half-life varied from approximately 12 to 16 days in rats and 6 to 11 days in monkeys. The pharmacokinetics of 13C5.5 was generally similar between female and male monkeys and rats.

13C5.5 was well tolerated in 4-week rat and 2-week monkey toxicology studies and had sufficient safety margins relative to the recommended starting dose for human clinical trials. The no-observed-adverse-effect-levels (NOAELs) during the repeat dose toxicology studies were 1500 mg/kg/dose via intravenous (IV) administration in rats and cynomolgus monkey and 200 mg/kg/dose via subcutaneous (SC) administration in cynomologus monkey.

This study was a Phase 1 first-in-human study in adult subjects with or without mild to moderate controlled asthma. This placebo-controlled study evaluated 4 single escalating doses (0.3, 1.0, 3.0, and 10.0 mg/kg) of 13C5.5 administered IV and 2 doses (0.3 and 3.0 mg/kg) of 13C5.5 administered as 3 weekly SC doses.

A study of 13C5.5 conducted in healthy subjects and subjects with mild-to-moderate controlled asthma allowed for collection of standard data regarding human pharmacokinetics and bioavailability of 13C5.5 as well as the tolerability, safety, and immunogenicity with single- and multiple-escalating doses of 13C5.5 in the target disease indication.

Experimental Protocol

This was a Phase 1, single and multiple escalating dose, placebo-controlled, double-blind, randomized, 3-part study which was conducted according to a sequential design. Adults in general good health (n=20) and adults with mild to moderate controlled asthma (n=27) were selected to participate in the study according to the selection criteria. No more than one subject was dosed per cohort per day.

Part 1 of the study consisted of four groups (Groups 1 through 4), with 5 subjects in each group. For Part 1, after meeting the selection criteria, adults in general good health (n=20) were assigned to one of the following four single dose groups:

Group 1 (intravenous infusion of 0.3 mg/kg 13C5.5 or placebo),
Group 2 (intravenous infusion of 1.0 mg/kg 13C5.5 or placebo),
Group 3 (intravenous infusion of 3.0 mg/kg 13C5.5 or placebo), or
Group 4 (intravenous infusion of 10.0 mg/kg 13C5.5 or placebo).

Within each group, four subjects were randomized to receive 13C5.5 and one subject was randomized to receive placebo. Dose escalation took place for a new cohort after all subjects within a dose cohort had satisfactorily completed at least the minimum one-week safety assessments.

Part 2 of the study consisted of three groups (Groups 5 through 7), with 5 subjects randomized to each of Groups 5, 6 and 7. For Part 2, after meeting the selection criteria, adult subjects with mild-to-moderate controlled asthma (n=15) were assigned to one of three single dose groups:

Group 5 (intravenous infusion of 0.3 mg/kg 13C5.5 or placebo),
Group 6 (intravenous infusion of 3.0 mg/kg 13C5.5 or placebo), or
Group 7 (intravenous infusion of 10.0 mg/kg 13C5.5 or placebo).

Within Groups 5, 6 and 7, four subjects were randomized to receive 13C5.5 and one subject was randomized to receive placebo.

As shown in FIG. 4, dosing for a cohort in Part 2 was allowed to begin after all subjects of the same dose level in Part 1 and all lower dose levels in Part 2 had satisfactorily completed at least the minimum one-week safety assessments after the last dose.

Part 3 of the study consisted of two groups (Groups 8 and 9), with 6 subjects randomized to each of Groups 8 and 9. For Part 3, after meeting the selection criteria, adult subjects with mild to moderate controlled asthma (n=12) were assigned to one of two groups:

Group 8 (subcutaneous injection of 0.3 mg/kg 13C5.5 or placebo, three weekly doses) or
Group 9 (subcutaneous injection of 3.0 mg/kg 13C5.5 or placebo, three weekly doses).

Within Groups 8 and 9, four subjects were randomized to receive 13C5.5 and two subjects were randomized to receive placebo.

Dosing for cohorts in Part 3 was allowed to begin after all subjects within the same dose level in Part 2, and one dose level higher in Part 1 and all lower dose levels in Part 3 had satisfactorily completed at least the minimum one-week safety assessments after the last dose (FIG. 4).

The study was conducted in a double-blind manner such that the investigators and subjects were blinded to treatment assignments within each group. For evaluation of safety, the medical monitor was unblinded to treatment assignments. A diagram of the treatment groups is shown in Table 1.

TABLE 1

Treatment Groups

| Part | Group | Regimen | Number of Subjects |
|---|---|---|---|
| Part 1* Healthy Subjects | Group 1 | 0.3 mg/kg 13C5.5 IV or placebo | 5 (4:1) |
| | Group 2 | 1.0 mg/kg 13C5.5 IV or placebo | 5 (4:1) |
| | Group 3 | 3.0 mg/kg 13C5.5 IV or placebo | 5 (4:1) |
| | Group 4 | 10.0 mg/kg 13C5.5 IV or placebo | 5 (4:1) |
| Part 2*# Mild/Moderate Controlled Asthma | Group 5 | 0.3 mg/kg 13C5.5 IV or placebo | 5 (4:1) |
| | Group 6 | 3.0 mg/kg 13C5.5 IV or placebo | 5 (4:1) |
| | Group 7 | 10.0 mg/kg 13C5.5 IV or placebo | 5 (4:1) |
| Part 3*$ Mild/Moderate Controlled Asthma | Group 8 | 0.3 mg/kg 13C5.5 SC or placebo, 3 weekly doses | 6 (4:2) |
| | Group 9 | 3.0 mg/kg 13C5.5 SC or placebo, 3 weekly doses | 6 (4:2) |

*Dose escalation took place for a new cohort after all subjects within a cohort had satisfactorily completed at least the minimum one-week safety assessments.
Group 5 was dosed after completion of Group 1 and evaluation of adequate safety for that dosing cohort (minimum one-week safety assessments). A similar approach was taken with Group 6 after completion of Groups 3 and 5 and Group 7 after completion of Groups 4 and 6.
$Group 8 was dosed after completion of Groups 2 and 5 and evaluation of adequate safety for those dosing cohorts and evaluation of adequate safety (minimum one-week safety assessments). A similar approach was taken with Group 9 after completion of Groups 4, 6 and 8.

For Parts 1 and 2, study drug or placebo was administered on Study Day 1 for each dose group. For Part 3, study drug or placebo was administered on Study Days 1, 8, and 15 for each dose group. Study drug administration on Study Days 8 and 15 may have occurred within a 24-hour period of the scheduled dose in cohorts 8 and 9. A minimum of one week separated the different dose levels.

Subjects were confined to the study site and supervised for approximately 4 to 6 days if they were in an IV dose group (Parts 1 and 2) or approximately 6 to 8 days if they were in an SC dose group (Part 3). Confinement began in the afternoon, of the Baseline day which may have occurred anytime within a 3-day window (i.e., Study Day −3 to Study Day −1) prior to dosing on Study Day 1, and ended after the collection of the 48-hour blood samples (Study Day 3) for subject's enrolled in the IV dosing groups, or after the collection of the 96-hour blood sample (Study Day 5) for subject's enrolled in the SC dosing groups. Strenuous activity during confinement was not permitted.

In addition, subjects in Part 3 were confined to the study site on Study Days 8 and 15 for 24 hours. During confinement subjects received an SC dose of either 13C5.5 or placebo and were evaluated for vital signs, safety assessments, laboratory assessments, pharmacokinetics and ADA, Biomarker sampling, electrocardiograms (ECGs), and pulmonary function tests (PFTs).

Subjects received a standardized diet, providing approximately 30% of the daily calories from fat, no more than 45% of daily calories from carbohydrates, and providing approximately 1900 calories/day for all meals during confinement. The composition (protein, fat, carbohydrate, and total calories) of all meals was determined by a dietician, and a record was kept with the source documents. During confinement in each part of the study, the subjects consumed only the scheduled meals provided in the study and water to quench thirst. The subjects abstained from all other food and beverage.

For Parts 1 and 2, no food or beverage, except for water to quench thirst, was allowed on Study Day −1 from 8 hours prior to dosing until approximately 2 hours after completion of the dosing.

For Part 3, no food or beverage, except for water to quench thirst, was allowed on Study Days 1, 8, and 15 from 8 hours prior to dosing until approximately 2 hours after completion of the dosing on Study Day 1.

Inclusion Criteria

A subject was eligible for study participation if he/she met the following criteria:

1. Males or females and age was between 18 and 55 years, inclusive.
2. For Parts 2 and 3, a diagnosis of asthma for at least 6 months prior to Screening:
   Mild to moderate controlled asthmatic subjects as defined below
      Use of prescribed short acting beta agonists for no more than 4 puffs/week for symptomatic control of asthma
      Long acting beta agonists (LABA) may have been taken as prescribed if used concurrently with inhaled corticosteroids (ICS). LABA was not administered for 12 hours before the screening PFTs were performed and could resume at the completion of the testing
      If on ICS, up to a medium dose may have been used (defined as the equivalent of fluticasone MDS/HFA up to 440 mcg daily or fluticasone DPT up to 500 mcg daily)
3. For Parts 2 and 3, forced expiratory volume 1 ($FEV_1$) ≥70% at the Screening and Baseline visits.
4. For Parts 2 and 3, if on an ICS, a stable ICS dose for ≥4 weeks before Study Day 1 and dose was expected to remain stable throughout the study. Must have used ICS for at least 4 weeks before the screening visit.
5. For Parts 2 and 3, subjects with asthma had a positive methacholine challenge test result available by history (within the past 12 months) or demonstrated airway reversibility in pulmonary function measurements by demonstrating at least 12% increase in $FEV_1$ from best effort when tested at least 30 minutes after two to four inhalations of inhaled albuterol or nebulized albuterol (or equivalent short acting beta agonist). Up to 2 attempts could have been made at any one session to demonstrate reversibility. Subjects may have returned on another day for repeat testing if necessary. Reversibility or methacholine challenge test confirming reversibility may have been documented by medical record if performed within the past 12 months. A positive methacholine challenge was defined as a $PC_{20}$ at a dose of methacholine of ≤8.0 mg/mL using American Thoracic Society standards for pulmonary function testing (see Guidelines for Methacholine and Exercise Challenge Testing 1999. Am J. Respir. Crit. Care Med., Vol. 161, pp. 309-329, 2000).
6. For Parts 2 and 3, subjects had well-controlled asthma for at least 4 weeks prior to Study Day 1, as defined by:
   Asthma symptoms≤2 days/week (i.e., cough, wheezing, shortness of breath)
   Nighttime awakenings≤2 times during the prior 4-week period
   No interference with normal activity
   No more than 4 inhalations/week of a short acting beta agonists for asthma symptom control (excluding the prophylactic use for the prevention of exercise induced bronchospasm).
7. If female, the subject met one of the following criteria:
   Postmenopausal for at least two years,
   Surgically sterile (bilateral oophorectomy, bilateral tubal ligation, or hysterectomy). Females who had undergone tubal ligation were required to agree to use a second form of contraception starting on the first day of confinement until 160 days after study drug treatment which included:
   Intrauterine (IUD) devices
   Barrier methods (diaphragm with spermicide, or condom with spermicide)
   Injected, oral, transdermal, vaginal, or implanted methods of hormonal contraceptives
8. Females had negative results for pregnancy tests performed:
   At Screening on a serum specimen obtained within 28 days prior to Study Day 1 and at Baseline, which may have occurred anytime within a 3 day window (i.e., Study Day −3 to Study Day −1) prior to dosing Study Day 1.
9. If male, the subject was surgically sterile or practicing at least 1 of the following methods of birth control during the study and for 160 days after last study drug administration:
   Subject used condom and partner(s) used an IUD
   Subject used condom and partner(s) used oral, injected, or implanted methods of hormonal contraceptives
   Subject used condoms and partner(s) used barrier method (contraceptive sponge, diaphragm, or vaginal ring with spermicidal jellies or creams)
   Additionally, male subjects agreed to not donate sperm during the study and for 160 days after the last dose of study drug.
10. For Part 1, Body Mass Index (BMI) was 18 to 29, inclusive. For Parts 2 and 3, BMI was 18 to 34, inclusive. BMI was calculated as weight in kg divided by square of height in meters. Body weight did not exceed 120 kg.
11. A condition of general good health (other than mild-moderate controlled asthma and associated medical conditions such as mild-moderate allergic rhinitis, atopic dermatitis, and gastroesophageal reflux disease) based upon the results of a medical history, physical examination, vital signs, laboratory profile and a 12-lead electrocardiogram (ECG).
12. Voluntarily signed and dated an informed consent approved by an IRB, prior to the conduct of any screening or study-specific procedures.

Exclusion Criteria

A subject was not eligible for study participation if he/she met any of the following criteria:

1. Subjects was using LABA therapy without concurrent use of ICS.
2. For Parts 2 and 3, asthma exacerbation within 8 weeks of Study Day 1.
3. For Parts 2 and 3, upper respiratory tract infection within 4 weeks of Study Day 1.
4. For Parts 2 and 3, asthma exacerbation requiring systemic corticosteroids or any other reason for requiring systemic corticosteroids within 6 months of Study Day 1.

5. For Parts 2 and 3, asthma exacerbation requiring emergency room (ER) visit, hospitalization, or medical intervention within 6 months of Study Day 1.
6. History of clinically significant allergic reaction i.e. anaphylaxis (per the investigator) to any drug, biologic, food or vaccine.
7. History of major immunologic reaction to any IgG containing agent.
8. History of atopic dermatitis involving ≥10% of body surface area or requiring medical treatment other than use of low to medium potency topical corticosteroids or over-the-counter emollients within 6 months of Study Day 1.
9. History of diabetes (Type I or Type II) or a fasting serum glucose level suggestive of diabetes (fasting serum glucose≥126 mg/dL) at Screening.
10. History of an allergic reaction or significant sensitivity to constituents of study drug.
11. History of tuberculosis (TB) or listeriosis.
12. History of persistent chronic or active infections which required hospitalization or treatment with IV antibiotics, IV antivirals or IV antifungals within 30 days of Screening or oral antibiotics/antivirals within 14 days prior to Study Day 1.
13. Subjects were evaluated for latent TB infections. Subjects demonstrated absence of TB infection or exposure as evidenced by a negative chest X-ray and negative purified protein derivative (PPD) skin test.
14. Positive test result for hepatitis B surface antigen (HBsAg), hepatitis C virus antibody (HCV Ab), or HIV antibodies (HIV Ab).
15. Positive test result on schistosomiasis serology.
16. History of unexplained diarrhea or abdominal pain of greater than 2 weeks duration.
17. History of untreated parasitic infections.
18. History of genetic or acquired immune deficiency.
19. For Parts 2 and 3, use of any non-essential medications, vitamins and/or herbal supplements within the 2-week period prior to study drug administration. For Part 1, used any prescription, over-the-counter medications or herbal supplements within 2 weeks prior to study drug administration.
20. For Parts 2 and 3, subject had taken Xolair within 5 months of Study Day 1.
21. For Parts 2 and 3, subject had a change in immunotherapy dose in the 3 months prior to Baseline.
22. Received any drug by injection within 30 days or 5 half-lives (whichever was longer) prior to study drug administration.
23. Received any investigational product within 30 days or 5 half-lives (whichever was longer) prior to study drug administration.
24. History of cancer or lymphoproliferative disease other than a successfully treated non-metastatic cutaneous squamous cell or basal cell carcinoma.
25. History of epilepsy, any clinically significant cardiac, respiratory (except mild to moderate asthma), renal, hepatic, gastrointestinal, hematologic, rheumatologic, or psychiatric disease or disorder, non-healing wounds or recurrent poor wound healing, or any uncontrolled medical illness. In addition the following were excluded:
    Chronic obstructive pulmonary disease (COPD), congestive heart failure, pulmonary embolism, pulmonary infiltration with eosinophilia, current cough secondary to drugs, vocal cord dysfunctions.
26. History of cardiopulmonary Sudden Death in any first-degree relative.
27. Pregnant or breast-feeding female.
28. Recent (6-month) history of drug or alcohol abuse.
29. Received of any live vaccine within 3 months prior to study drug administration.
30. Positive screen for drugs of abuse, alcohol, or cotinine at Screening or on admission.
31. Chest X-ray at Screening indicating any clinically significant abnormality (including calcified granuloma and/or pleural scarring) as assessed by appropriate medical personnel.
32. Febrile illness within 14 days prior to dosing.
33. Subjects with baseline QTc interval by Friderica correction (QTcF)>450 msec for females and >430 msec for males.
34. Donated or lost a significant blood volume (including plasmapheresis) or received a transfusion of any blood product within 8 weeks prior to study drug administration.
35. Subject was a smoker, or had a history of smoking within the 6-month period preceding study drug administration.
36. Current enrollment in another clinical study.
37. Previous enrollment in this study.
38. Considered by the investigator or medical monitor, for any reason, to be an unsuitable candidate to receive 13C5.5.

Treatments Administered

For Parts 1 and 2, a single dose of 13C5.5 or 13C5.5 placebo (0.3, 1.0, 3.0, or 10.0 mg/kg) was administered intravenously to each subject in the morning on Study Day 1. For Part 3, a total of 3 doses of 13C5.5 or 13C5.5 placebo (0.3 or 3.0 mg/kg) were administered subcutaneously in the morning on Study Days 1, 8, and 15. For the IV infusion, an indwelling catheter was inserted into a vein prior to dosing and was flushed with 1 mL of 13C5.5 placebo. 13C5.5 or 13C5.5 placebo was administered intravenously by continuous infusion over approximately 120 minutes with the subjects in a supine position. Following the infusion, a 1 mL 13C5.5 placebo flush was administered, and the line was maintained for a minimum of 2 hours following the completion of the infusion with a 0.9% isotonic saline solution. Subjects remained in a supine position for at least 5 minutes before infusion and until 30 minutes after the end of infusion.

For the SC dose, the study drug was administered subcutaneously into the left upper quadrant of the abdomen, avoiding any blood vessels, thickening or tenderness of skin, scars, fibrous tissue, stretch marks, bruising, redness, nevi, or other skin imperfections. The subject remained in a supine position for at least 30 minutes following each injection.

Subjects were assigned to one of nine dose groups (Table 2). Within each IV infusion group, four subjects were randomized to receive 13C5.5 and one subject received placebo. Within each SC group, four subjects received 13C5.5 and two received placebo. Dose escalation took place for a new cohort only after all subjects within a dose cohort had satisfactorily completed the minimum one-week safety assessments.

TABLE 2

| | Investigational Product: 13C5.5 | |
|---|---|---|
| | Formulation | |
| | 13C5.5 | 13C5.5 Placebo |
| Dosage Form | Parenteral | Parenteral |
| Formulation | Solution for injection in PFS | Solution for injection in PFS |
| Strength (mg) | 100 mg per 1.0 mL | N/A |
| Mode of Administration | IV Infusion or SC injection | IV Infusion or SC injection |
| Bulk Product Lot Number | 09-023042 | 09-023043 |
| Manufacturing Site | Germany | Germany |
| Finishing lot | 09-024016 | 09-024017 |
| Retest Date | 31 Jan. 2011 | 31 Jan. 2011 |

PFS = pre-filled syringe;
N/A = Not applicable.

For IV dosing, study medication in the PFS was further diluted with 13C5.5 placebo and mixed in an injection syringe for administration. For SC dosing, no dilution was required, however material was transferred to injection syringes for administration. The study drug was stored at 2° to 8° C./36° to 46° F., protected from light, and was not frozen.

Method of Assigning Subjects to Treatment Groups

As they were enrolled in the study, healthy subjects in Part 1 of the study were assigned unique consecutive numbers beginning with 1101, 1201, 1301 and 1401 for Groups 1, 2, 3, and 4, respectively. Subjects with mild to moderate controlled asthma in Part 2 were assigned unique consecutive numbers beginning with 2501, 2601 and 2701 for Groups 5, 6 and 7, respectively. Subjects with mild to moderate controlled asthma in Part 3 were assigned unique consecutive numbers beginning with 3801 and 3901 for Groups 8 and 9, respectively. The subjects were randomly assigned to receive 13C5.5 or placebo. The randomization schedule was computer-generated before the start of the study.

Selection of Doses in the Study

The maximum recommended starting dose (MRSD) for the first-in-human (FIH) trial was calculated according to the US Food and Drug Administration (FDA) Guidance for Industry "Estimating the safe starting dose in the clinical trials for therapeutics in adult healthy volunteers." Per the guidance, MRSD for proteins with molecular weight (MW) >100,000 daltons that are administered IV, should be estimated by normalizing across species in mg/kg, rather than using body surface area scaling. Additionally, the 13C5.5 in vitro and in vivo data for human versus cynomolgus monkey rIL-13 or rat rIL-13 demonstrate a ~8-155-fold potency shift, respectively which was included in the final MRSD estimates.

Based on the no adverse event effect level (NOAEL) from the 2-week repeat dose cynomolgus monkey study, a safety factor of 10, and a 8-fold potency shift between monkey and human rIL-13 from in vivo pharmacology data, the MRSD was determined to be 19 mg/kg. Similarly based on the NOAEL from the 4 week repeat dose rat study, a safety factor of 10, and a 52-fold potency shift between rat and human rIL-13 from in vivo pharmacology data, the MRSD was determined to be 3 mg/kg. Furthermore, when a potency shift of 155-fold using the in vitro pharmacology data is used, the human MRSD was determined to be 1 mg/kg.

A range of doses were evaluated in this trial to establish dose-linearity, with the low dose selected to allow for an appropriate safety margin while minimizing the likelihood of immunogenicity. The high dose was chosen to evaluate the safety margin of high doses in both a healthy and controlled asthma population prior to proceeding into Phase 2 to enable appropriate dose ranging design in the proof-of-concept study. Safety and tolerability were established following single escalating doses prior to proceeding to multiple dosing. Subcutaneous multiple dosing was important for assessing bioavailability, potential exposure-response relationships in the asthmatic population, and immunogenicity.

Prior and Concomitant Therapy

For Part 1, concomitant medications were not to be permitted throughout the study.

For Parts 2 and 3, short acting beta agonist use as rescue therapy was permitted during the study. Low to medium dose ICS use, and nasal corticosteroid use was permitted during the study. Long-acting beta agonist use was allowed for patients as prescribed if LABA was being used concurrently with ICS at Screening. There should have been no plan to change asthma medications for the duration of the study.

Systemic corticosteroid use was permitted if needed for control of an asthma exacerbation but subjects were to be discontinued from any further treatment with 13C5.5. Subjects who required use of systemic corticosteroids were to remain in the study and followed for safety assessments.

Only essential medications needed for the treatment of existing medical conditions were allowed during the study. These included lipid-lowering agents, anti-hypertensives, antacids, histamine-2 receptor antagonists, proton pump inhibitors, and pain relievers such as aspirin or non-steroidal anti-inflammatory drugs (NSAIDs). Antihistamine use, over-the-counter emollient use, and/or low to medium potency topical corticosteroid (Class IV, V, VI or VII) use was permitted in subjects with atopic dermatitis meeting entry criteria. Nasal corticosteroid use was permitted in subjects with allergic rhinitis. Subjects were on stable doses of permitted medications for a minimum of 8 weeks prior to Study Day 1 and remained on stable doses throughout the study. Use of acetaminophen of 2 g or less per day was allowed on an intermittent basis at the discretion of the investigator.

Use of non-essential medications was discouraged but if a subject reported taking any over-the-counter or prescription medications, vitamins and/or herbal supplements or if administration of any medication became necessary from 30 days prior to study drug administration through the end of the study, the name of the medication, dosage information including dose and frequency, date(s) of administration including start and end dates, and reason for use were recorded, and the medical monitor was notified.

13C5.5 and ADA Assay

Blood samples for 13C5.5 assay and anti-drug antibody (ADA) were obtained throughout the study, as indicated in Table 3. The time that each blood sample was collected was recorded to the nearest minute in the source document and on the appropriate electronic case report form (eCRF). The timing of blood collections took priority over all other scheduled study activities except for dosing.

Additional blood samples for drug measurement may have been collected from subjects if they were discontinued due to adverse events; the clock time, and date the sample was taken were to be recorded.

Samples were to be collected within ±5 minutes of the scheduled times on Study Day 1, within ±1 hour of the scheduled times on Study Days 2 through 6, and within ±3 hours of the scheduled times on Study Days 7 through 127.

TABLE 3

Serum Volume (mL) for Each Sample

IV Doses

| | | Hour | | | | | | |
|---|---|---|---|---|---|---|---|---|
| | 0 | 2 | 3, 4, 6, 10, 14, 24, 48, 72, 96, 120, 168 | 336 | 504 | 672 | 1008 | 1344, 2016, 2688 |
| 13C5.5 (MSD) | 1.5 | 1.5 | 1.5 | 1.5 | 1.5 | 1.5 | 1.5 | 1.5 |
| ADA (screening assay) | 1.5 | | | 1.5 | | 1.5 | | 1.5 |
| ADA (neutralizing assay) | 2.0 | | | 2.0 | | 2.0 | | 2.0 |

SC Doses

| | | Hour | | | |
|---|---|---|---|---|---|
| | 0 | 8, 24, 48, 72, 96, 120, 168, | 336 | 360, 384, 408, 432, 456, 504 | 672, 1008, 1344, 2016, 2352, 3024 |
| 13C5.5 (MSD) | 1.5 | 1.5 | 1.5 | 1.5 | 1.5 |
| ADA (screening assay) | 1.5 | | 1.5 | | 1.5 |
| ADA (neutralizing assay) | 2.0 | | 2.0 | | 2.0 |

MSD = Meso-scale-discovery assay.

Results from MSD assay for 13C5.5 and screening assay for ADA were reported for this study.

Blood samples for the 13C5.5 assay were collected by venipuncture into appropriately labeled evacuated serum collection tubes without gel separator. For IV study drug administration (Parts 1 and 2), samples for 13C5.5 assay were collected at 0 hour (pre-dose) and at 2, 3, 4, 6, 10, 14, 24, 48, 72, 96, 120, 168, 336, 504, 672, 1008, 1344, 2016, and 2688 hours following the onset of study drug administration on Study Day 1. For SC study drug administration (Part 3), samples for 13C5.5 assay were collected at 0 hour (pre-dose) and at 8, 24, 48, 72, 96, 120, 168, 336, 360, 384, 408, 432, 456, 504, 672, 1008, 1344, 2016, 2352 and 3024 hours following study drug administration on Study Day 1. The samples for hours 168 and 336 were collected immediately prior to dosing on Study Days 8 and 15, respectively. A blood sample for 13C5.5 assay was obtained at the early termination visit, if applicable. The serum volume needed for each sample is listed in Table 3. Blood was allowed to clot for 30 minutes at room temperature before centrifugation.

Blood samples for ADA assay were collected by venipuncture into appropriately labeled evacuated serum collection tubes without gel separator. For IV study drug administration, blood samples for ADA assay were collected on Study Day 1 at 0 hour (pre-dose) and on Study Days 15, 29, 57, 85 and 113. For SC study drug administration, blood samples for ADA assay were collected on Study Days 1 and 15 at 0 hour (pre-dose) and on Study Days 29, 43, 57, 85, 99 and 127. A blood sample for ADA assay was also obtained at the early termination visit, if applicable. The serum volume needed for each sample is listed in Table 3. Blood was allowed to clot for 30 minutes at room temperature before centrifugation.

Pharmacokinetic Variables

Values for the pharmacokinetic parameters of 13C5.5 after IV dosing were estimated using noncompartmental methods.

The maximum observed serum concentration ($C_{max}$) and the time to $C_{max}$ (peak time, $T_{max}$) were determined directly from the serum concentration-time data.

The value of the apparent terminal phase elimination rate constant (β, Beta) was obtained from the slope of the least squares linear regression of the logarithms of the serum concentration versus time data from the terminal log-linear phase of the profile. The terminal log-linear phase was identified using Phoenix™ WinNonlin® Version 6.1 (Pharsight Corporation, Mountain View, Calif.) and visual inspection. A minimum of three concentration-time data points was used to determine β. The actual times used for each subject may be found in the tables of the calculated pharmacokinetic parameters. The terminal phase elimination half-life ($t_{1/2}$) was calculated as $\ln(2)/\beta$.

The area under the plasma concentration-time curve (AUC) from time 0 to the time of the last measurable concentration ($AUC_t$) was calculated by the linear trapezoidal rule. The AUC was extrapolated to infinite time by dividing the last measurable plasma concentration ($C_t$) by β. Denoting the extrapolated portion of the AUC by $AUC_{ext}$, the AUC from time 0 to infinite time ($AUC_\infty$, $AUC_{inf}$) was calculated as follows:

$$AUC_\infty = AUC_t + AUC_{ext}$$

The percentage of the contribution of the extrapolated AUC ($AUC_{ext}$) to the overall $AUC_\infty$ was calculated by dividing the $AUC_{ext}$ by the $AUC_\infty$ and multiplying this quotient by 100.

The clearance value (CL) was calculated by dividing the administered dose by the $AUC_\infty$. The volume of distribution ($Vd_\beta$, VDB) value was calculated by dividing the CL by β. An estimate of the volume of distribution at steady state ($V_{ss}$) was also presented.

Dose-normalized $C_{max}$, $AUC_t$ and $AUC_\infty$ were also calculated for all groups in Parts 1 and 2.

For the SC dose groups in Part 3, $C_{max}$, $T_{max}$, and AUC from 0 to 168 hours post-dose ($AUC_{0-168}$) were estimated after the first and third doses. Beta and $t_{1/2}$ were estimated following the third SC dose. Additionally, dose-normalized $C_{max}$ and $AUC_{0-168}$ were calculated for Groups 8 and 9 in Part 3. The accumulation ratio (Rac) for the $AUC_{0-168}$ for Study Day 15 relative to the $AUC_{0-168}$ for Study Day 1 was also calculated.

Pharmacokinetics

For each of Parts 1, 2 and 3, serum concentrations of 13C5.5 and ADA and pharmacokinetic parameter values were tabulated for each subject and each dose group, and summary statistics were computed for each sampling time and each parameter.

For all the 13C5.5 single-dose regimens (groups) in healthy subjects (Part 1), analyses were performed on dose-normalized $C_{max}$, dose-normalized AUC, $T_{max}$ and 13 to address the issue of linear pharmacokinetics and dose proportionality. The logarithmic transformation was employed for $C_{max}$ and AUC. For each parameter, a one-way analysis of variance (ANOVA) was performed. Subjects were classified by dose level. Body weight or another measure of size was to be included as a covariate in the model for $C_{max}$ and AUC if the regression coefficient was statistically significant at level of 0.10. Within the framework of the final model, the highest dose was compared to the lowest dose. For the logarithms of $C_{max}$ and AUC, a 95% confidence interval, as well as a point estimate, were provided for the ratio of the central value of the highest dose relative to that of the lowest dose. The point estimate and the 95% confidence interval were obtained by exponentiation of the corresponding estimate and confidence limits for the difference of logarithm means. If at least four 13C5.5 dose levels were studied, a test was also performed at significance level 0.05 on a contrast in the dose level means, with the contrast chosen to be sensitive to an approximately linear trend with the logarithm of dose.

ANOVAs were also conducted for the single dose regimens in subjects with mild to moderate controlled asthma (Part 2). Within the framework of the model, the hypothesis of no difference between the highest and lowest doses was tested. The analyses could or could not have been performed jointly (analyses were not performed jointly) for the two populations (healthy subjects and subjects with mild to moderate controlled asthma). If analyses had been performed jointly for the two populations, then only data from the dose levels that the two populations had in common, were to be included. In this case, the model would have had effects for population, dose level and the interaction of population by dose level. Body weight or another measure of size could have been included in the model for $C_{max}$ and AUC. If the statistic on population-dose interaction had been significant at level of 0.10, then estimates and other inferences would have been provided for each population separately. Otherwise, estimates and other inferences were to have been based on the dose level main effects.

ANOVA was also performed for the multiple-dose regimens (Part 3) for pharmacokinetic parameters corresponding to those of the single-dose regimens. The decision on whether to include a measure of size as a covariate was based in part on the results for Parts 1 and 2. For $C_{max}$ and AUC, point estimates and 95% confidence intervals were provided for the ratio of the central values of the two doses, as explained for Part 1.

Missing Values and Model Violations

If there had been missing values due to premature discontinuations that were possibly related to study drug, the possibility of bias as a result of the missing values would have been considered.

Values of pharmacokinetic variables ($C_{max}$, AUC, etc.) are normally determined without replacing missing individual concentration values, simply using the available data, and, if necessary, performing the analysis with some missing values for a pharmacokinetic variable. However, missing concentration values for isolated individual serum samples could have been replaced (imputed) if such might have affected study conclusions or meaningfully affected point estimates.

If the probability distribution of a variable had non-symmetry to the degree that conclusions from the ANOVA (ANOVAs were performed for all parts rather than ANCOVAs) might have been affected or point estimates were misleading, then a transformation (an alternative to the logarithm in the case of $C_{max}$ and AUC) that yielded an approximately symmetric distribution was to have been sought. If a satisfactory transformation could not have been found or if it appeared that both tails of the probability distribution were quite long, a nonparametric analysis could have been performed. If the dose levels had unequal variances to the extent that conclusions might have been affected, then approximate methods that allowed for unequal variances would have been used.

Example 1: Escalating Single Doses in Healthy and Asthma Subjects (Groups 1 Through 7)

The mean±standard deviation (SD) serum concentration-time profiles after a single IV infusion of 0.3 mg/kg to 10 mg/kg 13C5.5 to healthy subjects (Groups 1 through 4) are presented in FIGS. 5 and 6 on linear and log-linear scales, respectively. The mean±SD serum concentration-time profiles after a single IV infusion of 0.3 mg/kg, 3.0 mg/kg or 10 mg/kg 13C5.5 to healthy subjects and subjects with mild to moderate asthma (Groups 1, 3 through 7) are presented in FIGS. 7 and 8 on linear and log-linear scales, respectively.

The mean±SD pharmacokinetic parameters of 13C5.5 after a single IV infusion of 13C5.5 to healthy and asthma subjects are shown in Table 4.

TABLE 4

Mean ± SD Pharmacokinetic Parameters of 13C5.5 Following a Single IV Infusion of 13C5.5 in Healthy Subjects and Asthma Subjects

| PK Parameter | Unit | Group 1 0.3 mg/kg (N = 4) Healthy Volunteer | Group 5 0.3 mg/kg (N = 4) Mild/Mod Asthma | Group 2 1.0 mg/kg (N = 3)[#] Healthy Volunteer | Group 3 3.0 mg/kg (N = 3)[#] Healthy Volunteer | Group 6 3.0 mg/kg (N = 4) Mild/Mod Asthma | Group 4 10 mg/kg (N = 4) Healthy Volunteer | Group 7 10 mg/kg (N = 4) Mild/Mod Asthma |
|---|---|---|---|---|---|---|---|---|
| $C_{max}$[†] | µg/mL | 6.88 ± 0.49 | 6.72 ± 0.91 | 20.65 ± 2.43 | 80.15 ± 6.11 | 68.55 ± 10.46 | 214.50 ± 27.77 | 292.00 ± 19.88 |
| $AUC_t$[†] | µg · hr/mL | 2102 ± 495 | 1999 ± 450 | 6490 ± 1192 | 26214 ± 5519 | 24580 ± 2578 | 82527 ± 8957 | 92307 ± 9810 |
| $AUC_\infty$[†] | µg · hr/mL | 2264 ± 394 | 2123 ± 544 | 6649 ± 1362 | 27180 ± 6051 | 25037 ± 2913 | 87342 ± 10966 | 94917 ± 9276 |
| $t_{1/2}$[§] | day | 17.35 ± 3.34 | 17.24 ± 8.24 | 18.83 ± 4.83 | 22.64 ± 4.26 | 16.37 ± 6.35 | 26.66 ± 4.52 | 23.50 ± 4.45 |

TABLE 4-continued

Mean ± SD Pharmacokinetic Parameters of 13C5.5 Following a
Single IV Infusion of 13C5.5 in Healthy Subjects and Asthma Subjects

| PK Parameter | Unit | Group 1 0.3 mg/kg (N = 4) Healthy Volunteer | Group 5 0.3 mg/kg (N = 4) Mild/Mod Asthma | Group 2 1.0 mg/kg (N = 3)[#] Healthy Volunteer | Group 3 3.0 mg/kg (N = 3)[#] Healthy Volunteer | Group 6 3.0 mg/kg (N = 4) Mild/Mod Asthma | Group 4 10 mg/kg (N = 4) Healthy Volunteer | Group 7 10 mg/kg (N = 4) Mild/Mod Asthma |
|---|---|---|---|---|---|---|---|---|
| $CL^\dagger$ | mL/hr/kg | 0.135 ± 0.022 | 0.148 ± 0.035 | 0.154 ± 0.028 | 0.114 ± 0.027 | 0.121 ± 0.013 | 0.116 ± 0.015 | 0.106 ± 0.010 |
| $Vd_\beta^\dagger$ | mL/kg | 82.4 ± 12.6 | 96.6 ± 25.9 | 102.0 ± 11.9 | 89.2 ± 7.6 | 72.8 ± 16.7 | 108.9 ± 18.1 | 89.0 ± 19.7 |
| $V_{ss}^\ddagger$ | mL/kg | 80.3 ± 4.5 | 90.0 ± 20.0 | 95.1 ± 7.3 | 83.1 ± 7.0 | 75.9 ± 15.9 | 97.7 ± 13.8 | 69.7 ± 7.8 |
| $C_{max}$/Dose | μg/mL/(mg/kg) | 22.93 ± 1.65 | 22.41 ± 3.02 | 20.65 ± 2.43 | 26.72 ± 2.04 | 22.85 ± 3.49 | 21.45 ± 2.78 | 29.20 ± 1.99 |
| $AUC_t$/Dose | μg · hr/mL/(mg/kg) | 7007 ± 1650 | 6664 ± 1501 | 6490 ± 1192 | 8738 ± 1840 | 8193 ± 859 | 8253 ± 896 | 9231 ± 981 |
| $AUC_\infty$/Dose | μg · hr/mL/(mg/kg) | 7546 ± 1315 | 7076 ± 1812 | 6649 ± 1362 | 9060 ± 2017 | 8346 ± 971 | 8734 ± 1097 | 9492 ± 928 |

[#]N = 4 for $C_{max}$ and $C_{max}$/Dose for Groups 2 and 3.
[‡]Harmonic mean ± pseudo-standard deviation; evaluations of $t_{1/2}$ were based on statistical tests for β.
[†]Parameter was not tested statistically.
$V_{ss}$: Estimate of volume of distribution at steady state.

Following IV administration, the exposures, as determined by AUC and $C_{max}$, appeared to increase in a dose dependent manner over the 0.3 mg/kg to 10 mg/kg range. Exposures (AUC and $C_{max}$) to 13C5.5 in healthy and asthma subjects were similar at the tested doses (0.3 mg/kg, 3.0 mg/kg, and 10.0 mg/kg IV). The pharmacokinetics of 13C5.5 were similar to that of a typical immunoglobulin G1 (IgG1) with a small volume of distribution and long half-life. Harmonic mean±pseudo SD half-lives of 13C5.5 ranged from 16.4±6.35 days to 26.7±4.52 days, and mean $Vd_\beta$ ranged from 72.8 to 108.9 mL/kg following IV infusions over the 0.3 mg/kg to 10.0 mg/kg dose range.

The total variabilities in $C_{max}$, $AUC_t$ and $AUC_\infty$ for 13C5.5 expressed as percent CV for escalating 13C5.5 single IV infusions in healthy and asthma subjects are shown in Table 5.

TABLE 5

Total Variability for Pharmacokinetic Parameters (Parts 1 and 2)

| | | Variability (% CV) | | | |
|---|---|---|---|---|---|
| Parameter | (Units) | Group 1 0.3 mg/kg (N = 4) | Group 2 1.0 mg/kg (N = 3)[#] | Group 3 3.0 mg/kg (N = 3)[#] | Group 4 10 mg/kg (N = 4) |
| | | Healthy Subjects | | | |
| $C_{max}$ | μg/mL | 7.2 | 11.8 | 7.6 | 12.9 |
| $AUC_t$ | μg · hr/mL | 23.5 | 18.4 | 21.1 | 10.9 |
| $AUC_\infty$ | μg · hr/mL | 17.4 | 20.5 | 22.3 | 12.6 |
| | | Mild to Moderate Asthma Subjects | | | |
| | | Group 5 0.3 mg/kg (N = 4) | Group 6 3.0 mg/kg (N = 4) | Group 7 10 mg/kg (N = 4) | |
| $C_{max}$ | μg/mL | 13.5 | 15.3 | 6.8 | |
| $AUC_t$ | μg · hr/mL | 22.5 | 10.5 | 10.6 | |
| $AUC_\infty$ | μg · hr/mL | 25.6 | 11.6 | 9.8 | |

[#]N = 4 for $C_{max}$ for Groups 2 and 3.

Example 2: Dose Proportionality and Pharmacokinetic Linearity in Healthy and Asthma Subjects (Parts 1 and 2)

The mean±SD dose-normalized $C_{max}$ and $AUC_\infty$ values for 13C5.5 following administration of single IV infusions of 13C5.5 over the 0.3 to 10 mg/kg dose range are presented in Table 4. The mean±SD dose-normalized $C_{max}$ and $AUC_\infty$ values of 13C5.5 versus dose level are presented in FIG. 9.

To address the issues of pharmacokinetic linearity and dose proportionality in healthy subjects and subjects with mild to moderate asthma, an ANOVA was performed on the pharmacokinetic parameters. Subjects were classified by treatment group (regimen).

In healthy subjects, 13C5.5 pharmacokinetics were dose linear in $C_{max}$ and AUC. The mean $C_{max}$, $AUC_t$ or $AUC_\infty$ values were similar between the highest dose (10 mg/kg) and the lowest dose (0.3 mg/kg). There were no statistically significant trends (p>0.05) for changes in 13C5.5 dose-normalized $C_{max}$, or dose-normalized AUC over the dose range (0.3 to 10 mg/kg). However, the power of the tests was low due to small number of subjects in each of the dose groups. Based on statistical tests for β, the $t_{1/2}$ value for the highest dose (26.7±4.52 days, 10 mg/kg) was statistically significantly longer than the value of 17.4±3.34 days for the lowest dose of 0.3 mg/kg (Table 4). The results also indicated that there were statistically significant trends (p<0.05) for increases in 13C5.5 $t_{1/2}$ across the 0.3 to 10 mg/kg dose range.

In subjects with mild to moderate asthma, the dose-normalized $C_{max}$ of the highest dose (10 mg/kg) was statistically significantly higher than that for the lowest dose of 0.3 mg/kg. The dose-normalized $AUC_t$ and $AUC_\infty$ values of the highest dose were statistically significantly greater (p<0.05) than those of the lowest dose. However, the observed departure from dose proportionality was small with an estimate of the ratio of central values of 1.3 for $C_{max}$ and 1.4 for AUC over a 33-fold range of doses.

Example 3: Three Weekly SC Injections in Asthma Subjects (Groups 8 and 9)

The mean±SD serum concentration versus time profiles of 13C5.5 following 3 weekly SC doses of 13C5.5 for Group 8 (0.3 mg/kg) and Group 9 (3.0 mg/kg) are presented in FIG. 10 on linear and log-linear scales.

The mean±SD pharmacokinetic parameters of 13C5.5 following three weekly doses of 0.3 mg/kg or 3.0 mg/kg 13C5.5 SC are shown in Table 6. The accumulation following 3 weekly doses of 13C5.5 appears to be linear as the $C_{max}$ and AUC values are approximately 3-fold greater following three 0.3 mg/kg or 3.0 mg/kg weekly doses of 13C5.5. $T_{max}$ appears to be similar following the first and third 0.3 and 3.0 mg/kg doses of 13C5.5. The harmonic mean±pseudo-SD half-life for 13C5.5 was 27.29±3.33 and 24.30±1.23 days after SC administration of 0.3 and 3.0 mg/kg for three days, respectively. Using simultaneous pharmacokinetic modeling of IV and SC data, the estimated bioavailability of 13C5.5 was approximately 70%.

at Hour 672 and Hour 96, respectively. For these two subjects, pharmacokinetic parameters were not calculated except for $C_{max}$ and $T_{max}$. Subject 1103 prematurely discontinued from the study and his last assay blood sample was collected at approximately 894 hours post dose. For this subject, pharmacokinetic parameters were calculated. The

TABLE 6

Mean ± SD Pharmacokinetic Parameters of 13C5.5 Following 3 Weekly SC Doses of 13C5.5 in Asthma Subjects

| Pharmacokinetic Parameter | Unit | Group 8 | | | Group 9 | | |
|---|---|---|---|---|---|---|---|
| | | 0.3 mg/kg, (Dose 1) (N = 4) | 0.3 mg/kg, (Dose 3) (N = 4) | Dose 3/Dose 1 Rac | 3.0 mg/kg, (Dose 1) (N = 4) | 3.0 mg/kg, (Dose 3) (N = 4) | Dose 3/Dose 1 Rac |
| $C_{max}$ | µg/mL | 1.80 ± 0.72 | 4.87 ± 0.97 | — | 17.90 ± 5.91 | 47.08 ± 12.54 | — |
| $AUC_{0\text{-}168}$ | µg · hr/mL | 236 ± 106 | 678 ± 107 | 3.19 | 2278 ± 1083 | 6875 ± 1343 | 3.29 |
| $T_{max}^{£}$ | hr | 108 (48-168) | 84 (49-120) | — | 108 (72-168) | 108 (48-169) | — |
| $t_{1/2}^{¢}$ | day | — | 27.29 ± 3.33 | — | — | 24.30 ± 1.23 | — |
| $C_{max}$/Dose | µg/mL/(mg/kg) | 6.01 ± 2.40 | 16.23 ± 3.23 | — | 5.97 ± 1.97 | 15.69 ± 4.18 | — |
| $AUC_{0\text{-}168}$/Dose | µg · hr/mL/(mg/kg) | 788 ± 353 | 2259 ± 355 | — | 759 ± 361 | 2292 ± 448 | — |

Rac: Accumulation ratio, calculated as the ratio of Day 15 $AUC_{0\text{-}168}$ to Day 1 $AUC_{0\text{-}168}$.
£Median (minimum-maximum).
¢Harmonic mean ± pseudo SD.

The total variabilities in $C_{max}$ and $AUC_{0\text{-}168}$ for 13C5.5 expressed as percent CV following administration of three weekly SC doses of 13C5.5 in subjects with mild to moderate asthma are shown in Table 7.

TABLE 7

Total Variability for Pharmacokinetic Parameters (Part 3)

| | | Variability (% CV), Mild to Moderate Asthma Subjects | | | |
|---|---|---|---|---|---|
| | | Group 8 0.3 mg/kg SC (N = 4) | | Group 9 3.0 mg/kg SC (N = 4) | |
| Parameter | (Units) | Day 1 | Day 15 | Day 1 | Day 15 |
| $C_{max}$ | µg/mL | 39.9 | 19.9 | 33.0 | 26.6 |
| $AUC_{0\text{-}168}$ | µg · hr/mL | 44.8 | 15.7 | 47.6 | 19.5 |

Example 4: Dose Proportionality and Pharmacokinetic Linearity (Part 3)

The mean±SD dose-normalized $C_{max}$ and AUC∞ values for 13C5.5 following administration of 3 weekly SC doses of 13C5.5 0.3 or 3.0 mg/kg are presented in Table 6. The mean±SD dose-normalized $C_{max}$ and AUC∞ values of 13C5.5 versus dose level are presented in FIGS. 11 and 12, respectively.

To address the issues of pharmacokinetic linearity and dose proportionality an ANOVA was performed on the pharmacokinetic parameters. Subjects were classified by treatment group (regimen).

In subjects with mild to moderate asthma administered 3 weekly SC doses, 13C5.5 pharmacokinetics were dose linear in $C_{max}$ and AUC. The mean $T_{max}$, $C_{max}$ and $AUC_{0\text{-}168}$ values were similar between the highest dose (3.0 mg/kg) and the lowest dose (0.3 mg/kg) on both Day 1 and Day 15. Of note, the power of the tests was low due to small number of subjects in each of the dose groups.

Statistics/Analysis for Examples 1-4

Adjustments for covariates were not performed.

Subjects 1202 and 1304 prematurely discontinued from the study and their last assay blood samples were collected few cases of a missing concentration for an individual sampling time did not prevent a determination of values of the pharmacokinetic parameters in which there is confidence.

Subjects whose available data warranted determination of values for the pharmacokinetic parameters were included in the statistical analysis. This study was conducted at a single study center; therefore, no considerations for a plurality of centers were necessary.

Conclusion for Examples 1-4

The pharmacokinetics of 13C5.5 after single dose administration were consistent with that of a IgG1 with a long half-life and small volume of distribution. For subjects administered a single IV infusion of 13C5.5, the systemic exposure (AUC and $C_{max}$) to 13C5.5 increased in a dose proportional manner over the dose range of 0.3 to 10 mg/kg for healthy subjects; however, for subjects with mild to moderate controlled asthma, AUC and $C_{max}$ increased in a slightly more (30 to 40%) than dose proportional manner over the same 33-fold dose range. For subjects with mild to moderate asthma administered 3 weekly SC doses, 13C5.5 pharmacokinetics were dose linear in both AUC and $C_{max}$ between the 0.3 and 3.0 mg/kg doses. The accumulation of 13C5.5 was as expected about 3-fold following three weekly SC doses.

During the study, 13C5.5 was well tolerated and safe when administered as a single dose up to 10 mg/kg IV or as multiple doses of 0.3 and 3 mg/kg SC. The adverse event profile in healthy adults was similar to that observed in subjects with asthma. No dose-related increases or administration-specific trends in treatment-emergent adverse events were appreciated. In each part of the study, the proportion of subjects reporting an upper respiratory tract infection or viral upper respiratory tract infection was greater among those receiving 13C5.5 compared to those receiving placebo. All of these events were of mild or moderate severity, and none were judged by the investigator to be possibly or probably related to study drug. However, the incidence of respiratory infections will continue to be monitored closely in future studies. Multiple events of blood CPK increased were reported including in one placebo subject; these events occurred following the initial confinement at the study site and were associated in each case with transient elevations in CPK and a history of increased physical activity.

One subject in the 13C5.5 0.3 mg/kg treatment group experienced a serious adverse event of hospitalization for bunionectomy that was assessed by the investigator as not related to study drug administration. No subjects discontinued study drug due to a treatment-emergent adverse event. Other than a report of infusion site pain in one subject, there were no adverse events of infusion-related reactions reported, and a review of events that could represent deterioration in asthma and spirometry data did not suggest a worsening of underlying disease in asthma subjects.

No clinically significant trends were detected in other safety analyses including vital signs, ECG variables and laboratory measurements.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating mild to moderate asthma in a human subject comprising subcutaneously administering to the human subject an anti-IL-13 antibody, or antigen-binding portion thereof, comprising a heavy chain variable region as set forth in SEQ ID NO:2 and a light chain variable region as set forth in SEQ ID NO:3 at a dose of about 0.3 mg/kg, wherein
   (a) a half-life of between about 24 and 31 days;
   (b) a $T_{max}$ of between about 3 and about 5 days;
   (c) a bioavailability of at least about 60%,
   (d) a clearance rate of between about 0.08 to about 0.14 mL/hr/kg; and
   (e) a volume of distribution of between about 55 to about 100 mL/kg,
is achieved following administration of the antibody, or antigen-binding portion thereof to said human subject.

2. The method of claim 1, wherein the anti-IL-13 antibody, or antigen-binding portion thereof, is administered once.

3. The method of claim 1, wherein the anti-IL-13 antibody, or antigen-binding portion thereof, is administered weekly.

4. The method of claim 3, wherein the antibody, or antigen-binding portion thereof, is administered for 3 weeks.

5. The method of claim 1, further comprising administering an additional agent to said human subject.

6. The method of claim 5, wherein said additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

7. A method of treating mild to moderate asthma in a human subject comprising subcutaneously administering to the human subject an anti-IL-13 antibody, or antigen-binding portion thereof, comprising a heavy chain variable region as set forth in SEQ ID NO:2 and a light chain variable region as set forth in SEQ ID NO:3 at a dose of about 3 mg/kg, wherein
   (a) a half-life of between about 23 and 26 days;
   (b) a $T_{max}$ of less than or equal to about 5 days;
   (c) a bioavailability of at least about 60%,
   (d) a maximum serum concentration ($C_{max}$) of between about 12 and about 60 μg/mL, and
   (e) an area under the serum concentration-time curve (AUC) of between about 1,100 and about 8,100 μgh/mL, is achieved following administration of the antibody, or antigen-binding portion thereof to said human subject.

8. The method of claim 7, wherein the anti-IL-13 antibody, or antigen-binding portion thereof, is administered once.

9. The method of claim 7, wherein the anti-IL-13 antibody, or antigen-binding portion thereof, is administered weekly.

10. The method of claim 9, wherein the antibody, or antigen-binding portion thereof, is administered for 3 weeks.

11. The method of claim 7, further comprising administering an additional agent to said human subject.

12. The method of claim 11, wherein said additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

* * * * *

```
SEQUENCE LISTING

<160> NUMBER OF SEQ ID NOS: 3

<210> SEQ ID NO 1
<211> LENGTH: 132
<212> TYPE: PRT
<213> ORGANISM: Homo sapiens

<400> SEQUENCE: 1

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80
```

```
                                   -continued

Val Leu Lys Leu Thr Ser Val Asp Pro Val Asp Thr Ala Thr Tyr Tyr
                85              90              95

Cys Ala Arg Thr Val Ser Ser Gly Tyr Ile Tyr Ala Met Asp Tyr
            100             105             110

Trp Gly Gln Gly Thr Leu Val Thr Val Ser Ser
        115             120

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gly Gly Thr Lys Val Glu Ile Lys
            100                 105
```